United States Patent
Carling et al.

(10) Patent No.: US 6,872,720 B2
(45) Date of Patent: Mar. 29, 2005

(54) PYRAZOLO-TRIAZINE DERIVATIVES AS LIGANDS FOR GABA RECEPTORS

(75) Inventors: William Robert Carling, Bishops Stortford (GB); Andrew Mitchinson, Sawbridgeworth (GB); Michael Geoffrey Russell, Welwyn Garden (GB); Leslie Joseph Street, Little Hallingbury (GB)

(73) Assignee: Merck Sharp & Dohme Ltd., Hoddesdon ( * ) Notice: Subject to any disclaimer, the term of this patent is extended or adjusted under 35 U.S.C. 154(b) by 109 days.

(21) Appl. No.: 10/240,971

(22) PCT Filed: Apr. 4, 2001

(86) PCT No.: PCT/GB01/01548

§ 371 (c)(1),
(2), (4) Date: Oct. 7, 2002

(87) PCT Pub. No.: WO01/77111

PCT Pub. Date: Oct. 18, 2001

(65) Prior Publication Data

US 2003/0060467 A1 Mar. 27, 2003

(30) Foreign Application Priority Data

Apr. 7, 2000 (GB) .............................. 0008696

(51) Int. Cl.[7] ...................... C07D 487/04; A61K 31/53; A61P 25/22
(52) U.S. Cl. ....................... 514/243; 544/183
(58) Field of Search ................................ 544/813, 184; 514/243

(56) References Cited

FOREIGN PATENT DOCUMENTS

| WO | WO 98/04559 | 2/1998 |
|---|---|---|
| WO | WO 98/15553 | 4/1998 |
| WO | WO 99/18104 | 4/1999 |
| WO | WO 00/12505 | 3/2000 |
| WO | WO 00/23449 | 4/2000 |
| WO | WO 01/14337 | 3/2001 |

OTHER PUBLICATIONS

Aartman et al. Community Dent Oral Epidemiol. 28(6): 435–42.*

Trapani G. et al: *European Journal of Medicinal Chemistry, Chimica Therapeutica*, Fr. Editions Scientifique Elsevier, Paris, vol. 31, No. 7, 1996, pp. 575–587.

Guerrini G. et al: *European Journal of Medicinal Chemistry, Chimica Therapeutica*, F., Editions Scientifique Elsevier, Paris, vol. 31, No. 4, 1996, pp. 259–272.

Krogsgaard–Larsen, et al: *Journal of Medicinal Chemistry*, US, American Chemical Society, vol. 37, No. 16, Aug. 5, 1994, pp. 2489–2505.

Martin, I. L. et al: *Exp. Opin. Ther. Patents*, vol. 9, No. 10, 1999, pp. 1347–1358.

* cited by examiner

*Primary Examiner*—Richard L. Raymond
*Assistant Examiner*—Venkataraman Balasubramanian
(74) *Attorney, Agent, or Firm*—J. Eric Thies; Melvin Winokur

(57) ABSTRACT

A class of substituted pyrazolo[1,5-d][1,2,4]triazine derivatives, possessing an optionally substituted cycloalkyl, phenyl or heteroaryl substituent at the 7-position, an alkyl group at the 4-position, and a substituted alkoxy moiety at the 2-position, are selective ligands for $GABA_A$ receptors, in particular having high affinity for the $\alpha 2$ and/or $\alpha 3$ subunit thereof, and are accordingly of benefit in the treatment and/or prevention of disorders of the central nervous system, including anxiety and convulsions.

8 Claims, No Drawings

PYRAZOLO-TRIAZINE DERIVATIVES AS LIGANDS FOR GABA RECEPTORS

CROSS REFERENCE TO RELATED APPLICATIONS

This application is a U.S. National Phase application under 35 U.S.C. §371 of PCT Application No. PCT/GB01/01548, filed Apr. 4, 2001, which claims priority under 35 U.S.C. §119 from GB Application No. 0008696.7, filed Apr. 7, 2000.

The present invention relates to a class of substituted pyrazolo-triazine derivatives and to their use in therapy. More particularly, this invention is concerned with substituted pyrazolo[1,5-d][1,2,4]triazine derivatives which are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six α subunits, four β subunits, three γ subunits, one δ subunit, one ε subunit and two ρ subunits.

Although knowledge of the diversity of the $GABA_A$ receptor gene family represents a huge step forward in our understanding of this ligand-gated ion channel insight into the extent of subtype diversity is still at an early stage. It has been indicated that an α subunit, a β subunit and a γ subunit constitute the minimum requirement for forming a fully functional $GABA_A$ receptor expressed by transiently transfecting cDNAs into cells. As indicated above, δ, ε and ρ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one α, one β and one γ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, α1β2γ2, α2β2/3γ2, α3β2/3, α2βγ1, α5β3γ2/3, α6βγ2, α6βδ and α4βδ. Subtype assemblies containing an α1 subunit are present in most areas of the brain and are thought to account for over 40% of $GABA_A$ receptors in the rat. Subtype assemblies containing α2 and α3 subunits respectively are thought to account for about 25% and 17% of $GABA_A$ receptors in the rat. Subtype assemblies containing an α5 subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the α1 subunit in combination with a β subunit and γ2. This is the most abundant $GABA_A$ receptor subtype, and is believed to represent almost half of all $GABA_A$ receptors in the brain.

Two other major populations are the α2βγ2 and α3βγ2/3 subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain α5-containing subtype assemblies. The physiological role of these subtypes has hitherto been unclear because no sufficiently selective agonists or antagonists were known.

It is now believed that agents acting as BZ agonists at α1βγ2, α2βγ2 or α3βγ2 subunits will possess desirable anxiolytic properties. Compounds which are modulators of the benzodiazepine binding site of the $GABA_A$ receptor by acting as BZ agonists are referred to hereinafter as "$GABA_A$ receptor agonists". The α1-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the α1 subunit. Accordingly, it is considered that $GABA_A$ receptor agonists which interact more favourably with the α2 and/or α3 subunit than with α1 will be effective in the treatment of anxiety with a reduced propensity to cause sedation. Also, agents which are antagonists or inverse agonists at α1 might be employed to reverse sedation or hypnosis caused by α1 agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as post-operative nausea and vomiting; eating disorders including anorexia nervosa and bulimia nervosa; premenstrual syndrome; muscle spasm or spasticity, e.g. in paraplegic patients; and hearing loss. Selective ligands for $GABA_A$ receptors may also be effective as pre-medication prior to anaesthesia or minor procedures such as endoscopy, including gastric endoscopy.

The present invention provides a class of pyrazolo-triazine derivatives which possess desirable binding properties at various $GABA_A$ receptor subtypes. The compounds in accordance with the present invention have good affinity as ligands for the α2 and/or α3 subunit of the human GABA$_A$ receptor. The compounds of this invention may interact more favourably with the α2 and/or α3 subunit than with the α1 subunit. Desirably, the compounds of the invention will exhibit functional selectivity in terms of a selective efficacy for the α2 and/or α3 subunit relative to the α1 subunit.

The compounds of the present invention are GABA$_A$ receptor subtype ligands having a binding affinity (K$_i$) for the α2 and/or α3 subunit, as measured in the assay described hereinbelow, of 100 nM or less, typically of 50 nM or less, and ideally of 10 nM or less. The compounds in accordance with this invention may possess at least a 2-fold, suitably at least a 5-fold, and advantageously at least a 10-fold, selective affinity for the α2 and/or α3 subunit relative to the α1 subunit. However, compounds which are not selective in terms of their binding affinity for the α2 and/or α3 subunit relative to the α1 subunit are also encompassed within the scope of the present invention; such compounds will desirably exhibit functional selectivity in terms of a selective efficacy for the α2 and/or α3 subunit relative to the α1 subunit.

The present invention provides a compound of formula I, or a salt or prodrug thereof

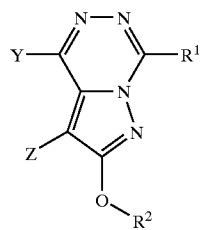

(I)

wherein

Y represents C$_{1-6}$ alkyl;

Z represents halogen; or C$_{1-6}$ alkyl, C$_{3-7}$ cycloalkyl, C$_{4-7}$ cycloalkenyl, C$_{6-8}$ bicycloalkyl, aryl, C$_{3-7}$ heterocycloalkyl, heteroaryl or di(C$_{1-6}$)alkylamino, any of which groups may be optionally substituted;

R$^1$ represents C$_{3-7}$ cycloalkyl, phenyl, furyl, thienyl, pyridinyl or pyrazinyl, any of which groups may be optionally substituted; and R$^2$ represents C$_{3-7}$ cycloalkyl(C$_{1-6}$)alkyl, aryl(C$_{1-6}$)alkyl or heteroaryl(C$_{1-6}$)alkyl, any of which groups may be optionally substituted.

The groups Z, R$^1$ and R$^2$ may be unsubstituted, or substituted by one or more substituents, suitably by one, two or three substituents, and more particularly by one or two substituents. In general, the groups Z, R$^1$ and R$^2$ will be unsubstituted or monosubstituted. Examples of optional substituents on the groups Z, R$^1$ and R$^2$ include C$_{1-6}$ alkyl, aryl(C$_{1-6}$)alkyl, pyridinyl(C$_{1-6}$)alkyl, halogen, halo(C$_{1-6}$) alkyl, dihalo(C$_{1-6}$)alkyl, trifluoromethyl, cyano, cyano(C$_{1-6}$)alkyl, hydroxy, hydroxymethyl, C$_{1-6}$ alkoxy, C$_{3-7}$ cycloalkyl(C$_{1-6}$)alkoxy, cyano(C$_{1-6}$)alkoxy, C$_{3-7}$ cycloalkoxy, amino, amino(C$_{1-6}$)alkyl, di(C$_{1-6}$)alkyl, N-(C$_{1-6}$)alkyl, di(C$_{1-6}$)alkylaminocarbonyl(C$_{1-6}$)alkyl, N-(C$_{1-6}$)alkylpiperidinyl, pyrrolidinyl(C$_{1-6}$)alkyl, piperazinyl(C$_{1-6}$)alkyl, morpholinyl(C$_{1-6}$)alkyl, di-(C$_{1-6}$) alkylmorpholinyl(C$_{1-6}$)alkyl and imidazolyl(C$_{1-6}$)alkyl. Representative substituents include C$_{1-6}$ alkyl, halogen, halo (C$_{1-6}$)alkyl, dihalo(C$_{1-6}$)alkyl, trifluoromethyl, cyano, C$_{1-6}$ alkoxy, cyano(C$_{1-6}$)alkoxy, C$_{3-7}$ cycloalkoxy, amino and di(C$_{1-6}$)alkylamino(C$_{1-6}$)alkyl, especially C$_{1-6}$ alkyl or halo-gen. Specific substituents include methyl, ethyl, n-propyl, isopropyl, fluoro, chloro, fluoroethyl, difluoroethyl, trifluoromethyl, cyano, methoxy, ethoxy, cyanomethoxy, cyclobutyloxy, amino and dimethylaminomethyl especially methyl, ethyl or fluoro.

As used herein, the expression "C$_{1-6}$ alkyl" includes methyl and ethyl groups, and straight-chained or branched propyl, butyl, pentyl and hexyl groups. Particular alkyl groups are methyl, ethyl, n-propyl, isopropyl, tert-butyl and 1,1-dimethylpropyl. Derived expressions such as "C$_{1-6}$ alkoxy" are to be construed accordingly.

Typical C$_{3-7}$ cycloalkyl groups include cyclopropyl, cyclobutyl, cyclopentyl and cyclohexyl.

The expression "C$_{3-7}$ cycloalkyl(C$_{1-6}$)alkyl" as used herein includes cyclopropylmethyl, cyclobutylmethyl, cyclopentylmethyl and cyclohexylmethyl.

Typical C$_{4-7}$ cycloalkenyl groups include cyclobutenyl, cyclopentenyl and cyclohexenyl.

Typical C$_{6-8}$ bicycloalkyl groups include bicyclo[2.1.1] hexyl and bicyclo[2.2.1]heptyl.

Typical aryl groups include phenyl and naphthyl, preferably phenyl

The expression "aryl(C$_{1-6}$)alkyl" as used herein includes benzyl, phenylethyl, phenylpropyl and naphthylmethyl especially benzyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups. Further heteroaryl groups include [1,2,4] triazolo[1,5-α]pyridinyl, 5,6,7,8-tetrahydro[1,2,4]triazolo [1,5-α]pyridinyl and 5,6,7,8-tetrahydro-[1,2,4]triazolo[1,5-α]pyrazinyl groups.

The expression "heteroaryl(C$_{1-6}$)alkyl" as used herein includes furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl. The expression "heteroaryl(C$_{1-6}$)alkyl" as used herein further includes [1,2,4]triazolo[1,5-α]pyridinylmethyl, 5,6,7,8-tetrahydro[1,2,4]triazolo[1,5-α]pyridinylmethyl and 5,6,7,8-tetrahydro[1,2,4]triazolo[1,5-α]pyrazinylmethyl.

The term "halogen" as used herein includes fluorine, chlorine, bromine and iodine, especially fluorine or chlorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Typical values for the substituent Y include methyl and ethyl. In a preferred embodiment, Y is methyl. In another embodiment, Y is ethyl.

Suitably, the substituent Z in the compounds of formula I above represents halogen (e.g. bromo or iodo); or $C_{1-6}$ alkyl, $C_{3-7}$ cycloalkyl, aryl or heteroaryl, any of which groups may be optionally substituted. Suitably, Z may represent $C_{1-6}$ alkyl, $C_{3-7}$ cycloalkyl, aryl or heteroaryl, any of which groups may be optionally substituted. More particularly, Z may represent $C_{3-7}$ cycloalkyl or aryl either of which groups may be optionally substituted.

Suitable values for the substituent Z include tert-butyl, 1,1-dimethylpropyl, cyclobutyl, cyclopentyl, phenyl, pyridinyl, furyl and thienyl, any of which groups may be optionally substituted by one or more substituents.

Typical values of Z include tert-butyl, cyclopentyl, cyclohexyl, phenyl, furyl and thienyl, any of which groups may be optionally substituted by one or more substituents.

Particular values of Z include cyclopentyl and phenyl, either of which groups may be optionally substituted by one or more substituents.

Specific examples of optional substituents on the group Z include methyl, fluoro, chloro, trifluoromethyl, cyano and amino. Particular substituents include fluoro, chloro and trifluoromethyl, especially fluoro.

Typical examples of suitable values for the substituent Z include methyl, ethyl, isopropyl, tert-butyl, 1,1-dimethylpropyl, methyl-cyclopropyl, cyclobutyl, methyl-cyclobutyl, cyclopentyl, methyl-cyclopentyl, cyclohexyl, cyclobutenyl, bicyclo[2.1.1]hex-1-yl, bicyclo[2.2.1]hept-1-yl, phenyl, fluorophenyl, difluorophenyl,chlorophenyl, trifluoromethylphenyl, cyanophenyl, aminophenyl, pyrrolidinyl, methyl-pyrrolidinyl, piperidinyl, morpholinyl, thiomorpholinyl, pyridinyl, furyl, thienyl, chloro-thienyl and diethylamino.

Individual examples of Z include tert-butyl, cyclopentyl, cyclohexyl, phenyl, fluorophenyl, furyl and thienyl. Typically, Z represents cyclopentyl or fluorophenyl.

In a particular embodiment, the substituent Z represents $C_{3-7}$ cycloalkyl either unsubstituted or substituted by $C_{1-6}$ alkyl, especially methyl. Favourably, Z represents cyclobutyl, cyclopentyl or cyclohexyl, particularly cyclobutyl or cyclopentyl, especially cyclopentyl.

In another embodiment, Z represents tert-butyl.
In a further embodiment, Z represents phenyl.
In a still further embodiment, Z represents fluorophenyl.

In an additional embodiment, Z represents furyl or thienyl.

Suitable values of $R^1$ include phenyl thienyl and pyrazinyl, any of which groups may be optionally substituted by one or more substituents.

Examples of typical optional substituents on the group $R^1$ include methyl, fluoro, chloro and methoxy. Particular substituents include methyl, fluoro and methoxy, especially fluoro.

Specific values of $R^1$ include cyclopropyl, phenyl, methylphenyl, fluorophenyl, difluorophenyl, trifluorophenyl, chlorophenyl, methoxyphenyl, furyl, thienyl, methyl-thienyl, pyridinyl and pyrazinyl.

Individual values of $R^1$ include phenyl, fluorophenyl, difluorophenyl, trifluorophenyl, thienyl and pyrazinyl.

More particularly, $R^1$ may represent unsubstituted or monosubstituted phenyl. Most particularly, $R^1$ represents phenyl or fluorophenyl. In one specific embodiment, $R^1$ represents fluorophenyl.

Suitably, $R^2$ represents aryl($C_{1-6}$)alkyl or heteroaryl($C_{1-6}$)alkyl, either of which groups may be optionally substituted.

Suitable values for the substituent $R^2$ in the compounds according to the invention include cyclohexylmethyl, benzyl, pyrazolylmethyl, isoxazolylmethyl, thiazolylmethyl, thiazolylethyl, imidazolylmethyl, benzimidazolylmethyl, oxadiazolylmethyl, triazolylmethyl, tetrazolylmethyl, pyridinylmethyl, pyridazinylmethyl, pyrimidinylmethyl, pyrazinylmethyl, quinolinylmethyl, isoquinolinylmethyl, quinoxalinylmethyl, [1,2,4]triazolo[1,5-α]pyridinylmethyl, 5,6,7,8-tetrahydro[1,2,4]triazolo[1,5-α]pyridinylmethyl and 5,6,7,8-tetrahydro[1,2,4]triazolo[1,5-α]pyrazinylmethyl, any of which groups may be optionally substituted by one or more subsituents.

In one embodiment, $R^2$ represents triazolylmethyl or pyridinylmethyl, either of which groups may be optionally substituted by one or more substituents.

Suitably, $R^2$ represents an optionally substituted triazolylmethyl group.

Examples of suitable optional substituents on the group $R^2$ include $C_{1-6}$ alkyl, aryl($C_{1-6}$)alkyl, pyridinyl($C_{1-6}$)alkyl, halogen, halo($C_{1-6}$)alkyl, dihalo($C_{1-6}$)alkyl, cyano, cyano ($C_{1-6}$)alkyl, hydroxymethyl, $C_{1-6}$ alkoxy, $C_{3-7}$ cycloalkyl ($C_{1-6}$)alkoxy, cyano($C_{1-6}$)alkoxy, $C_{3-7}$ cycloalkoxy, amino ($C_{1-6}$)alkyl, di($C_{1-6}$)alkylamino($C_{1-6}$)alkyl, di($C_{1-6}$) alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl ($C_{1-6}$)alkyl and di($C_{1-6}$)alkylmorpholinyl($C_{1-6}$)alkyl, especially $C_{1-6}$ alkyl.

Specific illustrations of particular substituents on the group $R^2$ include methyl, ethyl, n-propyl, isopropyl, benzyl, pyridinylmethyl, chloro, chloromethyl, fluoroethyl, difluoroethyl, cyano, cyanomethyl, hydroxymethyl, methoxy, ethoxy, cyclopropylmethoxy, cyanomethoxy, cyclobutyloxy, dimethylaminomethyl, aminoethyl, dimethylaminoethyl, dimethylaminocarbonylmethyl, N-methylpiperidinyl, pyrrolidinylethyl, piperazinylethyl, morpholinylmethyl and dimethylmorpholinylmethyl.

Selected substituents for the group $R^2$ include methyl, ethyl, n-propyl and isopropyl, especially methyl or ethyl.

Representative values of $R^2$ include hydroxymethyl-cyclohexylmethyl, cyanobenzyl, hydroxymethyl-benzyl dimethylaminomethyl-benzyl, pyrazolylmethyl, dimethyl-pyrazolylmethyl, methyl-isoxazolylmethyl, thiazolylmethyl, methyl-thiazolylmethyl, ethyl-thiazolylmethyl, methyl-thiazolylethyl, imidazolylmethyl, methyl-imidazolylmethyl, ethyl-imidazolylmethyl, benzyl-imidazolylmethyl, benzimidazolylmethyl, methyl-benzimidazolylmethyl, methyl-oxadiazolylmethyl, triazolylmethyl, methyl-triazolylmethyl, ethyl-triazolylmethyl, propyl-triazolylmethyl, isopropyl-triazolylmethyl, benzyl-triazolylmethyl, pyridinylmethyl-triazolylmethyl, fluoroethyl-triazolylmethyl, difluoroethyl-triazolylmethyl, cyanomethyl-triazolylmethyl, dimethylaminomethyl-triazolylmethyl, aminoethyl-triazolylmethyl, dimethylaminoethyl-triazolylmethyl, dimethylaminocarbonylmethyl-triazolylmethyl, N-methylpiperidinyl-triazolylmethyl, pyrrolidinylethyl-triazolylmethyl, piperazinylethyl-triazolylmethyl, morpholinylethyl-triazolylmethyl, methyl-tetrazolylmethyl, pyridinylmethyl, methyl-pyridinylmethyl, dimethyl-pyridinylmethyl, cyano-pyridinylmethyl, methoxy-pyridinylmethyl, ethoxy-pyridinylmethyl, cyclopropylmethoxy-pyridinylmethyl, cyanomethoxy-pyridinylmethyl, cyclobutyloxy-pyridinylmethyl, pyridazinylmethyl, chloro-pyridazinylmethyl, pyrimidinylmethyl, pyrazinylmethyl, quinolinylmethyl, isoquinolinylmethyl, quinoxalinylmethyl, [1,2,4]triazolo[1,5-α]pyridinylmethyl, 5,6,7,8-tetrahydro[1,2,4]triazolo[1,5-α]pyridinylmethyl and 5,6,7,8-tetrahydro[1,2,4]triazolo[1,5-α]pyrazinylmethyl.

Specific values of $R^2$ include methyl-triazolylmethyl and ethyl-triazolylmethyl.

In one embodiment, $R^2$ is methyl-triazolylmethyl. In another embodiment, $R^2$ is ethyl-triazolylmethyl.

A particular sub-class of compounds according to the invention is represented by the compounds of formula IIA, and salts and prodrugs thereof:

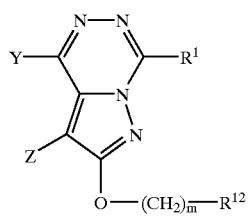

(IIA)

wherein

Y, Z and $R^1$ are as defined with reference to formula I above;

m is 1 or 2, preferably 1; and $R^{12}$ represents aryl or heteroaryl, either of which groups may be optionally substituted.

Suitably, $R^{12}$ represents phenyl, pyrazolyl, isoxazolyl, thiazolyl, imidazolyl, benzimidazol, oxadiazolyl, triazolyl, tetrazolyl, pyridinyl, pyridazinyl, pyrimidinyl, pyrazinyl, quinolinyl, isoquinolinyl, quinoxalinyl, [1,2,4]triazolo[1,5-α]pyridinyl, 5,6,7,8-tetrahydro[1,2,4]triazolo[1,5-α]pyridinyl or 5,6,7,8-tetrahydro[1,2,4]triazolo[1,5-α]pyrazinyl, any of which groups may be optionally substituted by or more substituents.

Suitable values of $R^{12}$ include triazolyl and pyridinyl, either of which groups may be optionally substituted by one or more substituents.

A particular value of $R^{12}$ is optionally substituted triazolyl.

Examples of typical substituents on the group $R^{12}$ include $C_{1-6}$ alkyl, aryl($C_{1-6}$)alkyl, pyridinyl($C_{1-6}$)alkyl, halogen, halo($C_{1-6}$)alkyl, dihalo($C_{1-6}$)alkyl, cyano, cyano($C_{1-6}$)alkyl, hydroxymethyl, $C_{1-6}$ alkoxy, $C_{3-7}$ cycloalkyl($C_{1-6}$)alkoxy, cyano($C_{1-6}$)alkoxy, $C_{3-7}$ cycloalkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl and di($C_{1-6}$)alkylmorpholinyl($C_{1-6}$)alkyl, especially $C_{1-6}$ alkyl, Illustrative values of specific substituents on the group $R^{12}$ include methyl, ethyl, n-propyl, isopropyl, benzyl, pyridinylmethyl, chloro, chloromethyl, fluoroethyl, difluoroethyl, cyano, cyanomethyl, hydroxymethyl, methoxy, ethoxy, cyclopropylmethoxy, cyanomethoxy, cyclobutyloxy, dimethylaminomethyl, aminoethyl, dimethylaminoethyl, dimethylaminocarbonylmethyl, N-methylpiperidinyl, pyrrolidinylethyl, piperazinylethyl, morpholinylethyl and dimethylmorpholinylmethyl.

Selected substituents for the group $R^{12}$ include methyl, ethyl, n-propyl, and isopropyl, especially methyl or ethyl.

Particular values of $R^{12}$ include cyanophenyl, hydroxymethyl-phenyl, dimethylaminomethyl-phenyl, pyrazolyl, dimethyl-pyrazolylmethyl-isoxazolyl, thiazolyl, methyl-thiazolyl, ethyl-thiazolyl, imidazolyl, methyl-imidazolyl, ethyl-imidazolyl, benzyl-imidazolyl, benzimidazolyl, methyl-benzimidazolyl, methyl-oxadiazolyl, triazolyl, methyl-triazolyl, ethyl-triazolyl, propyl-triazolyl, isopropyl-triazolyl, benzyl-triazolyl, pyridinylmethyl-triazolyl, fluoroethyl-triazolyl, difluoroethyl-triazolyl, cyanomethyl-triazolyl, dimethylaminomethyl-triazolyl, aminoethyl-triazolyl, dimethylaminoethyl-triazolyl, dimethylaminocarbonylmethyl-triazolyl, N-methylpiperidinyl-triazolyl, pyrrolidinylethyl-triazolyl, piperazinylethyl-triazolyl, morpholinylethyl-triazolyl, methyl-tetrazolyl, pyridinyl, methyl-pyridinyl, dimethyl-pyridinyl, cyano-pyridinyl, methoxy-pyridinyl, ethoxy-pyridinyl, cyclopropylmethoxy-pyridinyl, cyanomethoxy-pyridinyl, cyclobutyloxy-pyridinyl, pyridazinyl, chloro-pyridazinyl, pyrimidinyl, pyrazinyl, quinolinyl, isoquinolinyl, quinoxalinyl, [1,2,4]triazolo[1,5-α]pyridinyl, 5,6,7,8-tetrahydro-[1,2,4]triazolo[1,5-α]pyridinyl and 5,6,7,8-tetrahydro[1,2,4]triazolo[1,5-α]pyrazinyl.

Specific values of $R^{12}$ include methyl-triazolyl and ethyl-triazolyl.

In one embodiment, $R^{12}$ is methyl-triazolyl. In another embodiment, $R^{12}$ is ethyl-triazolyl.

A particular subset of the compounds of formula IIA above is represented by the compounds of formula IIB, and pharmaceutically acceptable salts thereof:

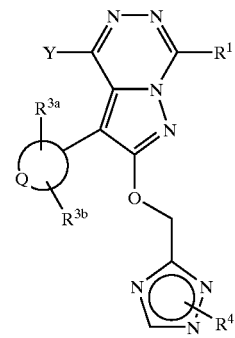

(IIB)

wherein

Y and $R^1$ are as defined with reference to formula I above;

Q represents the residue of a cyclopropyl, cyclobutyl, cyclopentyl, cyclohexyl, phenyl, pyridinyl, furyl or thienyl ring;

$R^{3a}$ represents hydrogen, methyl, fluoro, chloro, trifluoromethyl, cyano or amino;

$R^{3b}$ represents hydrogen or fluoro; and

R⁴ represents hydrogen, methyl, ethyl, n-propyl, isopropyl, fluoroethyl or difluoroethyl.

In relation to formula IIB above, R¹ suitably represents phenyl, fluorophenyl, difluorophenyl, trifluorophenyl, furyl, thienyl, pyridinyl or pyrazinyl, especially phenyl or fluorophenyl.

Suitably, Q represents the residue of a cyclopentyl, cyclohexyl, phenyl, furyl or thienyl ring.

In one embodiment of the compounds of formula IIB above, Q represents the residue of a cyclobutyl, cyclopentyl, phenyl, pyridinyl, furyl or thienyl ring. In a subset of this embodiment, Q represents the residue of a cyclopentyl or phenyl ring.

In a particular embodiment, Q suitably represents the residue of a cyclopentyl ring. In another embodiment, Q represents the residue of a phenyl ring.

Suitably, $R^{3a}$ represents hydrogen or fluoro, typically hydrogen.

Typically, $R^{3b}$ represents hydrogen.

Suitably, R⁴ represents methyl or ethyl.

Specific compounds within the scope of the present invention include;

3,7-bis(2-fluorophenyl)-4-methyl-2-(2-methyl-2H-[1,2,4] triazol-3-ylmethoxy)pyrazolo[1,5-d][1,2,4]triazine;
3-(2-fluorophenyl)-4-methyl-2-(2-methyl-2H-[1,2,4]triazol-3-ylmethoxy)-7-phenylpyrazolo[1,5-d][1,2,4]triazine;
3-cyclopentyl-2-(2-ethyl-2H-[1,2,4]triazol-3-ylmethoxy)-7-(2-fluorophenyl)-4-methylpyrazolo[1,5-d][1,2,4]triazine;
3-cyclopentyl-7-(2-fluorophenyl)-4-methyl-2-(2-methyl-2H-[1,2,4]triazol-3-ylmethoxy)pyrazolo[1,5-d][1,2,4]triazine;
3-cyclopentyl-2-(2-ethyl-2H-[1,2,4]triazol-3-ylmethoxy)-4-methyl-7-phenyl-pyrazolo[1,5-d][1,2,4]triazine;
3-cyclopentyl-4-methyl-2-(2-methyl-2H-[1,2,4]triazol-3-ylmethoxy)-7-phenylpyrazolo[1,5-][1,2,4]triazine;
3-tert-butyl-7-(2,6-difluorophenyl)-2-(2-ethyl-2H-[1,2,4] triazol-3-ylmethoxy)-4-methylpyrazolo[1,5-d][1,2,4] triazine;
3-tert-butyl-4-methyl-2-(2-methyl-2H-[1,2,4]triazol-3-ylmethoxy)-7-(2,3,6-trifluorophenyl)pyrazolo[1,5-d][1,2,4]triazine;
3-(2-fluorophenyl)-4-methyl-2-(2-methyl-2H-[1,2,4]triazol-3-ylmethoxy)-7-(pyrazin-2-yl)pyrazolo[1,5-d][1,2,4] triazine;
3,7-bis(2-fluorophenyl)-4-methyl-2-(1-methyl-1H-[1,2,4] triazol-3-ylmethoxy)pyrazolo[1,5-d][1,2,4]triazine;
2-(2-ethyl-2H-[1,2,4]triazol-3-ylmethoxy)-3-(2-fluorophenyl)-4-methyl-7-(thien-3-yl)pyrazolo [1,5-d][1,2,4]triazine;
3-(2-fluorophenyl)-4-methyl-2-(1-methyl-1H-[1,2,4]triazol-3-ylmethoxy)-7-(thien-3-yl)pyrazolo[1,5-d][1,2,4] triazine;
3-cyclohexyl-7-(2-fluorophenyl)-4-methyl-2-(2-methyl-2H-[1,2,4]triazol-3-ylmethoxy)pyrazolo[1,5-d][1,2,4] triazine;
7-(2-fluorophenyl)-4-methyl-2-(2-methyl-2H-[1,2,4]triazol-3-ylmethoxy)-3-(thien-3-yl)pyrazolo[1,5-d][1,2,4] triazine;
7-(2-fluorophenyl)-4-methyl-2-(2-methyl-2H-[1,2,4]triazol-3-ylmethoxy)-3-phenylpyrazolo[1,5-d][1,2,4]triazine;
7-(2-fluorophenyl)-3-(fur-3-yl)-4-methyl-2-(2-methyl-2H-[1,2,4]triazol-3-ylmethoxy)pyrazolo[1,5-d][1,2,4] triazine;
7-(2-fluorophenyl)-4-methyl-2-(1-methyl-1H-[1,2,4]triazol-3-ylmethoxy)-3-(thien-3-yl)pyrazolo[1,5-d][1,2,4] triazine;
7-(2-fluorophenyl)-4-methyl-2-(1-methyl-1H-[1,2,3]triazol-4-ylmethoxy)-3-(thien-3-yl)pyrazolo[1,5-d][1,2,4] triazine;
7-(4-fluorophenyl)-4-methyl-2-(2-methyl-2H-[1,2,4]triazol-3-ylmethoxy)-3-(thien-3-yl)pyrazolo[1,5-d][1,2,4] triazine;
7-(2,4-difluorophenyl)-4-methyl-2-(2-methyl-2H-[1,2,4] triazol-3-ylmethoxy)-3-(thien-3-yl)pyrazolo[1,5-d][1,2, 4]triazine;

and sats and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof.

The binding affinity ($K_i$) of the compounds according to the present invention for the α3 subunit of the human GABA$_A$ receptor is conveniently as measured in the assay described hereinbelow. The α3 subunit binding affinity ($K_i$) of the compounds of the invention is ideally 10 nM or less, preferably 2 nM or less, and more preferably 1 nM or less.

The compounds according to the present invention will ideally elicit at least a 40%, preferably at least a 50%, and more preferably at least a 60%, potentiation of the GABA EC$_{20}$ response in stably transfected recombinant cell lines expressing the α3 subunit of the human GABA$_A$ receptor. Moreover, the compounds of the invention will ideally elicit at most a 30%, preferably at most a 20%, and more preferably at most a 10%, potentiation of the GABA EC$_{20}$ response in stably transfected recombinant cell lines expressing the α1 subunit of the human GABA$_A$ receptor.

The potentiation of the GABA EC$_{20}$ response in stably transfected cell lines expressing the α3 and α1 subunits of the human GABA$_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk⁻ fibroblast cells.

The compounds according to the present invention exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pins, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula I as defined above may be prepared by a process which comprises cyclising a compound of formula III:

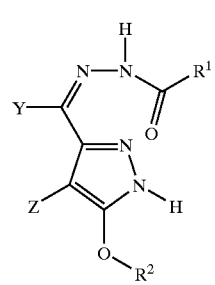

(III)

wherein Y, Z, $R^1$ and $R^2$ are as defined above.

The cyclisation of compound III may conveniently be effected by heating compound III to an elevated temperature, e.g. (i) a temperature in the region of 180–200° C., in the presence of a high-boiling medium such as Dowtherm A; or (ii) the reflux temperature of an inert solvent such as xylene, optionally in the presence of a proton source such as triethylamine hydrochloride.

The intermediates of formula III above may be prepared by reacting a compound of formula IV with a hydrazide derivative of formula V:

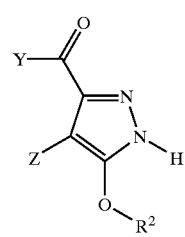

(IV)

(V)

wherein Y, Z, $R^1$ and $R^2$ are as defined above.

The reaction between compounds IV and V is conveniently effected by heating the reactants, optionally in the presence of a proton source such as triethylamine hydrochloride, typically at reflux in an inert solvent such as xylene.

In another procedure, the compounds of formula I as defined above may be prepared by a process which comprises reacting a compound of formula VI with a compound of formula VII:

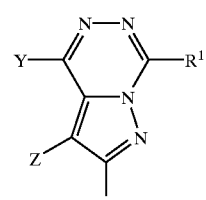

(VI)

$R^2 - L^1$ (VII)

$R^2 - L^1$ (VII)

wherein Y, Z, $R^1$ and $R^2$ are as defined above, and $L^1$ represents a suitable leaving group.

The leaving group $L^1$ is suitably a halogen atom, typically chloro.

The reaction between compounds VI and VII is conveniently effected by stirring the reactants in a suitable solvent, typically N,N-dimethylformamide, in the presence of a base such as cesium carbonate or potassium carbonate.

Similarly, the intermediates of formula IV may be prepared by reacting a compound of formula VII as defined above with a compound of formula VIII:

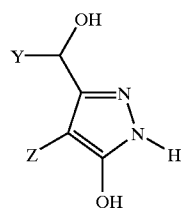

(VIII)

wherein Y and Z are as defined above; under conditions analogous to those described above for the reaction between compounds VI and VII; followed by oxidation.

Oxidation of the CHYOH side-chain in the intermediate resulting from the reaction between compounds VII and VII to the ketone YC═O side-chain in the corresponding intermediate of formula IV is suitably effected by treatment with pyridinium dichromate, in which case the reaction is conveniently carried out in dichloromethane at room temperature.

In a further procedure, the compounds of formula I as defined above may be prepared by a process which comprises reacting a compound of formula IX with a compound of formula X:

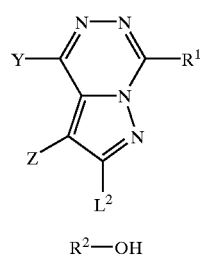

(IX)

R²—OH (X)

R²—OH (X)

wherein Y, Z, $R^1$ and $R^2$ are as defined above, and $L^2$ represents a suitable leaving group.

The leaving group $L^2$ is typically an arylsulfonyloxy moiety, e.g. p-toluenesulfonyloxy (tosyloxy).

The reaction between compounds IX and X is conveniently effected by stirring the reactants in a suitable solvent, typically N,N-dimethylformamide, in the presence of a base such as sodium hydride.

The intermediates of formula IX above may be prepared by reacting a compound of formula V as defined above with a compound of formula XI:

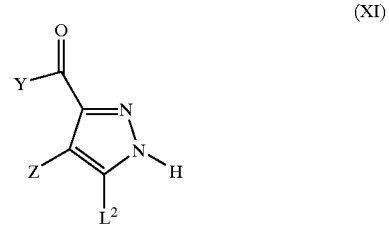

(XI)

wherein Y, Z and $L^2$ are as defined above.

The reaction between compounds V and XI is conveniently effected by heating the reactants, optionally in the presence of a proton source such as triethylamine hydrochloride, typically at reflux in an inert solvent such as xylene; followed if necessary by heating to a temperature in the region of 180° C. in the presence of a high-boiling medium such as Dowtherm A.

In a still further procedure, the compounds of formula I as defined above may be prepared by a process which comprises reacting a compound of formula XII with a compound of formula XIII:

Z—M (XII)

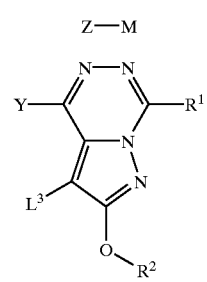

(XIII)

wherein Y, Z, $R^1$ and $R^2$ are as defined above, $L^3$ represents a suitable leaving group, and M represents —B(OH)$_2$ or a cyclic ester thereof formed with an organic diol, e.g. 1,3-propanediol or M represents —Sn(Alk)$_3$ in which Alk represents a $C_{1-6}$ alkyl group, typically n-butyl; in the presence of a transition metal catalyst.

The leaving group $L^3$ is typically a halogen atom, e.g. bromo.

Where M represents —B(OH)$_2$ or a cyclic ester thereof, the transition metal catalyst is suitably tris(dibenzylideneacetone)palladium(0), in which case the reaction between compounds XII and XIII is conveniently effected at an elevated temperature in a solvent such as 1,4-dioxane, typically in the presence of tri-tert-butylphosphine and cesium carbonate.

Where M represents —Sn(Alk)$_3$, the transition metal catalyst is suitably tetrakis(triphenylphosphine)palladium (0), in which case the reaction between compounds XII and XIII is conveniently effected at an elevated temperature in a solvent such as 1,4-dioxane, typically in the presence of copper(I) iodide.

The compounds of formula XIII above may be prepared by reacting a compound of formula VII as defined above with a compound of formula XIV:

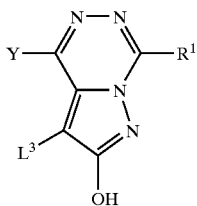

(XIV)

wherein Y, R¹ and L³ are as defined above; under conditions analogous to those described above for the reaction between compounds VI and VII.

The intermediates of formula XIV in which the leaving group L³ represents bromo may be prepared by bromination of a compound of formula XV:

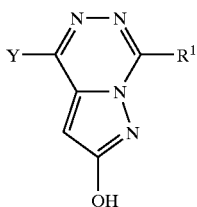

(XV)

wherein Y and R¹ are as defined above.

The bromination reaction is conveniently effected by treating the appropriate compound of formula XV with bromine, typically in glacial acetic acid.

The intermediates of formula VII and X above may be prepared by the procedures described in WO 98/04559, or by methods analogous thereto.

Where they are not commercially available, the starting materials of formula V, VI, VIII, XI, XII and XV may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. Indeed, as will be appreciated, the compounds of formula XIII in which L³ is halogen are compounds according to the invention in their own right. By way of example, a compound of formula I initially obtained wherein $R^2$ is unsubstituted may be converted into a corresponding compound wherein $R^2$ is substituted, typically by standard alkylation procedures, for example by treatment with a haloalkyl derivative in the presence of sodium hydride and N,N-dimethylformamide, or with a hydroxyalkyl derivative in the presence of triphenylphosphine and diethyl azodicarboxylate. Furthermore, a compound of formula I initially obtained wherein the $R^2$ substituent is substituted by a halogen atom, e.g. chloro, may be converted into the corresponding compound wherein the $R^2$ substituent is substituted by a di($C_{1-6}$)alkylamino moiety by treatment with the appropriate di($C_{1-4}$)alkylamine, typically with heating in a solvent such as 1,4-dioxane in a sealed tube.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [³H]-flumazenil to the benzodiazepine binding site of human $GABA_A$ receptors containing the α2 or α3 subunit stably expressed in Ltk⁻ cells.

Reagents

Phosphate buffered saline (PBS).

Assay buffer: 10 mM $KH_2PO_4$, 100 mM KCl, pH 7.4 at room temperature.

[³H]-Flumazenil (18 nM for α1β3γ2 cells; 18 nM for α2β3γ2 cells; 10 nM for α3β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [³H]-flumazenil (final concentration for α1β3γ2: 1.8 nM; for α2β3γ2: 1.8 nM; for α3β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scitillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [³H]-flumazenil from the α2 and/or α3 subunit of the human GABA$_A$ receptor of 100 nM or less.

EXAMPLE 1

3,7-Bis(2-fluorophenyl)-4-methyl-2-(2-methyl-2H-[1,2,4]triazol-3-ylmethoxy)pyrazolo[1,5-d][1,2,4]triazine a) 3-(2-Fluorophenyl)-4-hydroxy-5-methyl-5H-furan-2-one To 2-fluorophenylacetic acid (25 g, 0.16 mol) and methyl lactate (17 g, 0.16 mol) in THF (600 ml) was added 1,3-dicyclohexylcarbodiimide (34 g, 0.16 mol) and 4-dimethylaminopyridine (0.99 g, 8.1 mmol) at 5° C. The mixture was allowed to warm to room temperature and stirred under nitrogen overnight. The solvent was removed in vacuo, then the residue was taken up in diethyl ether (300 ml), and the resulting slurry was filtered to remove insoluble material. The filtrate was concentrated in vacuo, and the residual oil was dissolved in potassium tert-butoxide solution (162 ml of a 1.0 M solution in tert-butanol). The mixture was stirred at reflux for 16 h and was allowed to cool to room temperature. Water (300 ml) was added, and the solution was washed with diethyl ether (2×100 ml). The aqueous solution was acidified to pH 1 with 5 N hydrochloric acid. The product formed an immiscible oil, which solidified upon standing. This was collected by filtration, washed with water and dried at 50° C., yielding 3-(2-fluorophenyl)-4-hydroxy-5-methyl-5H-furan-2-one as a pale yellow solid (23.2 g). ¹H NMR (400 MHz, CDCl$_3$) δ 1.46 (3H, d, J=6.7 Hz), 5.00 (1H, q, J=6.7 Hz), 7.22 (2H, m), 7.39 (2H, m), 12.50 (1H, br s).

b) Toluene-4-sulfonic acid 4-(2-fluorophenyl)-5-(1-hydroxymethyl-1H-pyrazol-3-yl ester To 3-(2-fluorophenyl)-4-hydroxy-5-methyl-5H-furan-2-one (18.7 g, 90 mmol) in ethanol (90 ml) was added hydrazine hydrate (24 ml, 0.45 mol), and the mixture was stirred at reflux for 3 days. The solution was concentrated to approximately 30 ml, and was then stirred at 90° C. for 1 week. Hydrazine hydrate (24 ml, 0.45 mol) was added, and the mixture was stirred at 90° C. for another week. More hydrazine hydrate (24 ml, 0.45 mol) was added, and the solution was stirred as before for 1 week, and was then allowed to concentrate to approximately 30 mL Ethanol (90 ml) and hydrazine hydrate (24 ml, 0.45 mol) were added, and the mixture was heated at reflux for 1 week. The solvent was removed in vacuo, yielding a glassy foam. This was suspended in dichloromethane (200 ml) and tosyl chloride (20.4 g, 0.107 mol) and triethylamine (16.3 ml, 0.165 mol) were added at 5° C. The solution was allowed to warm to room temperature and was stirred overnight. The mixture was washed with saturated sodium chloride solution (1×100 ml), dried over magnesium sulfate, and was then concentrated in vacuo. The residue was purified by flash chromatography on silica gel (20 to 50% ethyl acetate in dichloromethane, UV detection), yielding toluene-4-sulfonic acid 4-(2-fluorophenyl)-5-(1-hydroxyethyl)-1H-pyrazol-3-yl ester as a yellow glass, which solidified upon standing (17.6 g). ¹H NMR (400 MHz, CDCl$_3$) δ 1.33 (3H, d, J=6.6 Hz), 2.38 (3H, s), 5.01 (1H, q, J=6.6 Hz), 6.98 (1H, m), 7.11 (3H, m), 7.27 (2H, m), 7.80 (2H, d, J=8.3 Hz), 10.30 (1H, br s); MS (ES⁺) m/e 377 [MH]⁺.

c) Toluene-4-sulfonic acid 5-acetyl-4-(2-fluorophenyl)-1H-pyrazol-3-yl ester

To toluene-4-sulfonic acid 4-(2-fluorophenyl)-5-(1-hydroxyethyl)-1H-pyrazol-3-yl ester (16.4 g, 43.6 mmol) in dichloromethane (500 ml) was added pyridinium dichromate (19.7 g, 52.3 mmol) and the resulting slurry was stirred at room temperature for 1 h. The mixture was poured directly onto a column of silica gel, and the product was eluted off with ethyl acetate, yielding toluene-4-sulfonic acid 5-acetyl-4-(2-fluorophenyl)-1H-pyrazol-3-yl ester as a yellow solid (8.64 g). ¹H NMR (400 MHz, CDCl$_3$) δ 2.16 (3H, s), 2.43 (3H, s), 7.09 (1H, m), 7.22 (3H, m), 7.34 (1H, m), 7.41 (1H, m), 7.65 (2H, d, J=6.8 Hz); MS (ES⁺) m/e 375 [MH]⁺.

d) Toluene-4-sulfonic acid 3,7-bis(2-fluorophenyl - 4-methylpyrazolo[1,5-d][1,2,4]triazin-2-yl ester Toluene-4-sulfonic acid 5-acetyl-4-(2-fluorophenyl)-1H-pyrazol-3-yl ester (8.26 g, 22.1 mmol) and 2-fluorobenzhydrazide (3.86 g, 25.0 mmol) were stirred together in xylene (250 ml) at reflux overnight. The solvent was removed in vacuo, and the residue was heated in Dowtherm A at 180° C. for 2 h. The mixture was poured directly onto a column of silica gel, and the Dowtherm was eluted off with dichloromethane before eluting the product off with 10% ethyl acetate in dichloromethane (UV detection). Toluene-4-sulfonic acid 3,7-bis(2-fluorophenyl)-4-methylpyrazolo[1,5-d][1,2,4]triazin-2-yl ester was obtained as a yellow solid (6.62 g). ¹H NMR (400 MHz, CDCl$_3$) δ 2.43 (3H, s), 2.53 (3H, s), 7.17–7.37 (6H, m), 7.41–7.51 (2H, m), 7.63 (1H, m), 7.69 (3H, m); MS (ES⁺) m/e 493 [MH]⁺.

e) 3,7-Bis(2-fluorophenyl)-4-methyl-2-(2-methyl-2H-[1,2,4]triazol-3-ylmethoxy)pyrazo[1,5-d][1,2,4]triazine To toluene-4-sulfonic acid 3,7-bis(2-fluorophenyl)-4-methylpyrazolo[1,5-d][1,2,4]triazin-2-yl ester (200 mg, 0.407 mmol) and (2-methyl-2H-[1,2,4]triazol-3-yl)methanol (57.5 mg, 0.0509 mmol; prepared as described in EP-A-170073) in DMF (5 ml) was added sodium hydride (23.7 mg of a 60% dispersion in mineral oil; 0.593 mmol) and the mixture was stirred at room temperature for 30 min. Water (50 ml) was added, then the solvent was removed in vacuo, and the residue was purified by flash chromatography on silica gel eluting with 0 to 100% ethyl acetate in dichloromethane. 3,7-Bis(2-fluorophenyl)-4-methyl-2-(2-methyl-2H-[1,2,4]triazol-3-ylmethoxy)pyrazolo[1,5-d][1,2,4]triazine was isolated as a gum, which solidified upon trituration under isohexane (75 mg). ¹H NMR (400 MHz, CDCl$_3$) δ 2.52 (3H, s), 3.73 (3H, s), 5.44 (1H, d, J=13 Hz), 5.49 (1H, d, J=13 Hz), 7.18–7.31 (3H, m), 7.36–7.46 (3H, m), 7.63 (1H, m), 7.78 (1H, m), 7.82 (1H, s); MS (ES⁺) m/e 434 [MH]⁺. Anal. Found C, 61.03; H, 4.08; N, 21.95%. $C_{22}H_{17}F_2N_7O \cdot 0.1\ C_6H_{14}$ requires C, 61.41; H, 4.20; N, 22.18%.

EXAMPLE 2

3-(2-Fluorophenyl)-4-methyl-2-(2-methyl-2H-[1,2,4]triazol-3-ylmethoxy)-7-phenylpyrazolo[1,5-d][1,2,4]triazine a) Toluene-4-sulfonic acid 3-(2-fluorophenyl)-4-methyl-7-phenylpyrazolo[1,5-d][1,2,4]triazin-2-yl ester Toluene-4-sulfonic acid 5acetyl-4-(2-fluorophenyl)-1H-pyrazol-3-yl ester (1.0 g, 2.7 mmol; prepared as described in Example 1, steps a to c) was stirred with benzhydrazide (400 mg, 2.9 mmol) in xylene (30 ml) at reflux overnight. The mixture was allowed to cool to room temperature. A solid crystallised out of solution This was separated by filtration, and was recrystallised from ethyl acetate, yielding toluene-4-sulfonic acid 3-(2-fluorophenyl)-4-methyl-7-phenylpyrazolo[1,5-d][1,2,4]triazin-2-yl ester as a white solid (694 mg). ¹H NMR (400 MHz, CDCl$_3$) δ 2.47 (3H, s), 2.52 (3H, s), 7.19 (1H, t, J=8.9 Hz), 7.28 (3H, m), 7.41–7.52 (4H, m), 7.61 (1H, m), 7.79 (2H, d, J=8.3 Hz), 8.25 (2H, d, J=7.5 Hz); MS (ES⁺) m/e 475 [MH]⁺.

b) 3-(2-Fluorophenyl)-4-methyl-2-(2-methyl-2H-[1,2,4]triazol-3-ylmethoxy)-7-phenylpyrazolo[1,5-d][1,2,4]triazine This compound was prepared using the procedure described in Example 1, step e, using toluene-4-sulfonic acid 3-(2-fluorophenyl)-4-methyl-7-phenylpyrazolo[1,5-d][1,2,4]triazin-2-yl ester instead of toluene-4-sulfonic acid 3,7-bis(2-fluorophenyl)-4-methylpyrazolo[1,5-d][1,2,4]triazin-2-yl ester. Data for the title compound: $^1$H NMR (400 MHz, CDCl$_3$) δ 2.61 (3H, s), 3.82 (3H, s), 5.56 (1H, d, J=13 Hz), 5.61 (1H, d, J=13 Hz), 7.19–7.28 (2H, m), 7.38 (1H, m), 7.44 (1H, m), 7.60 (3H, m), 7.86 (1H, s), 8.37 (2H, m); MS (ES$^+$) m/e 416 [MH]$^+$.

EXAMPLE 3

3-Cyclopentyl-2-(2-ethyl-2H-[1,2,4]triazol-3-ylmethoxy)-7-(2-fluorophenyl)-4-methylpyrazolo[1,5-d][1,2,4]triazine a) Toluene-4-sulfonic acid 4-cyclopentyl-5-(1-hydroxyethyl)-1H-pyrazol-3-yl ester To a solution of methyl lactate (6.9 g, 66.5 mmol) and pyridine (5.9 ml, 1.1 molar eq) in diethyl ether (200 ml) at 0° C. was added dropwise over 1 h 2-bromo-2-cyclopentylacetyl chloride (15 g, 1 molar eq). The reaction mixture was allowed to warm to room temperature and stirred for 14 h. The solution was washed with water (1×100 ml) and brine (1×100 ml), then dried (Na$_2$SO$_4$), filtered and concentrated in vacuo to leave an oil (18.7 g). This oil was dissolved in a solution of diethyl ether (56 ml) and trimethylsilyl chloride (224 ml) in the presence of zinc (18.33 g, 5 molar eq) and heated under reflux for 1 h with rapid stirring. After this time, the reaction mixture was cooled in an ice bath and water (200 ml) was added slowly and cautiously with rapid stirring. Then 4 N sodium hydroxide solution was added carefully until a pH of 14 was achieved and the aqueous layer was separated and washed with diethyl ether (1×200 ml). The aqueous layer was then acidified to pH 1 using conc. HCl and was extracted with dichloromethane (4×200 ml). The combined layers were dried (Na$_2$SO$_4$), filtered and evaporated under vacuum to give a crude tetronic acid (3.48 g). This was dissolved in ethanol (80 ml) and after the addition of hydrazine hydrate (1.9 ml, 2 molar eq) the reaction mixture was heated under reflux for 14 h. The solvents were removed by rotary evaporation under high vacuum to leave a crude pyrazolone (3.4 g). This was dissolved in dichloromethane (50 ml) with p-toluenesulfonyl chloride (3.3 g, 1 molar eq) and cooled to 0° C. whereupon triethylamine (2.88 ml, 1.2 molar eq) was added dropwise. The reaction mixture was allowed to warm to room temperature and stirred for 14 h. More dichloromethane (200 ml) was added to the solution which was then washed with brine (1×100 ml), dried (MgSO$_4$), filtered and evaporated under vacuum to give a crude product which was purified by chromatography on silica gel using 0 to 30% ethyl acetate in isohexane as eluent to give as a colourless oil toluene-4-sulfonic acid 4-cyclopentyl-5-(1-hydroxyethyl)-1H-pyrazol-3-yl ester (3.65 g). $^1$H NMR (360 MHz, CDCl$_3$) δ 1.49 (3H, d, J=6.6 Hz), 1.56–1.93 (8H, m), 2.45 (3H, s), 2.77 (1H, m), 5.03 (1H, q, J=6.6 Hz), 7.35 (2H, d, J=8.5 Hz), 7.90 (2H, d, J=8.5 Hz); MS (ES$^+$) m/e 351 [MH]$^+$.

b) Toluene-4-sulfonic acid 5-acetyl-4-cyclopentyl-1H-pyrazol-3-yl ester

To toluene-4-sulfonic acid 4-cyclopentyl-5-(1-hydroxyethyl)-1H-pyrazol-3-yl ester (3.65 g, 10.43 mmol) in dichloromethane (250 ml) was added pyridinium dichromate (3.92 g, 1 molar eq) and the resulting slurry was stirred at room temperature for 1 h. The mixture was poured directly onto a column of silica gel, and the crude product was eluted off with ethyl acetate. Evaporation and further purification on silica gel using 0 to 20% ethyl acetate in isohexane as eluent yielded toluene-4-sulfonic acid 5-acetyl-4cyclopentyl-1H-pyrazol-3-yl ester as a colourless oil (1.36 g). $^1$H NMR (400 MHz, CDCl$_3$) δ 1.62–1.91 (8H, m), 2.46 (3H, 8), 2.53 (3H, s), 3.26 (1H, m), 7.37 (2H, d, J=6.8 Hz), 7.90 (2H, d, J=6.8 Hz); MS (ES$^+$) m/e 349 [MH]$^+$.

c) Toluene-4-sulfonic acid 3-cyclopentyl-7-(2-fluorophenyl)-4-methylpyrazolo[1,5-d][1,2,4]triazin-2-yl ester Toluene-4-sulfonic acid 5-acetyl-4-cyclopentyl-1H-pyrazol-3-yl ester (0.65 g, 1.87 mmol) and 2-fluorobenzhydrazide (0.317 g, 1.1 molar eq) were stirred together in xylene (20 ml) at reflux for 2 h. The solvent was reduced to ~5 ml and Dowtherm A (20 ml) was added and the reaction mixture was heated at 180° C. for 3 h. The mixture was cooled and poured directly onto a column of silica gel, and the Dowtherm was eluted off with dichloromethane before eluting the product off with 3–5% ethyl acetate in dichloromethane (UV detection). Toluene-4-sulfonic acid 3-cyclopentyl-7-(2-fluorophenyl)-4-methylpyrazolo[1,5-d][1,2,4]triazin-2-yl ester was obtained as a light brown solid (0.5 g). $^1$H NMR (360 MHz, CDCl$_3$) δ 1.72–2.06 (8H, m), 2.42 (8H, s), 2.91 (3H, 8), 3.46 (1H, m), 7.16–7.33 (4H, m), 7.58–7.65 (2H, m), 7.84 (2H, d, J=8.7 Hz); MS (ES$^+$) m/e 467 [MH]$^+$.

d) 3-Cyclopentyl-2-(2-ethyl-2H-[1,2,4]triazol-3-ylmethoxy)-7-(2-fluorophenyl)-4-methylpyrazolo[1,5-d][1,2,4]triazine To toluene-4-sulfonic acid 3-cyclopentyl-7-(2-fluorophenyl)-4-methylpyrazolo[1,5-d][1,2,4]triazin-2-yl ester (230 mg, 0.494 mmol) and (2-ethyl-2H-[1,2,4]triazol-3-yl)methanol (75.6 mg, 1.2 molar eq; prepared as described in EP-A-170073) in DMF (10 ml) was added sodium hydride (22 mg of a 60% dispersion in mineral oil; 1.2 molar eq) and the mixture was stirred at room temperature for 1 h. Water (90 ml) was added then the solution was extracted with diethyl ether (4×50 ml). The combined ether layers were washed with brine (1×100 ml), dried (Na$_2$SO$_4$), the solvent was removed in vacuo and the residue was purified by flash chromatography on silica gel eluting with 0 to 50% ethyl acetate in dichloromethane. 3-Cyclopentyl-2-(2-ethyl-2H-[1,2,4]triazol-3-ylmethoxy)-7-(2-fluorophenyl)-4-methylpyrazolo[1,5-d][1,2,4]triazine was isolated as a gum, which solidified upon trituration under diethyl ether/isohexane (34.5 mg, mp =105° C.). $^1$H NMR (360 MHz, CDCl$_3$) δ 1.36 (3H, t, J=7.3 Hz), 1.53–1.91 (8H, m), 2.87 (3H, s), 3.41 (1H, m), 4.10 (2H, q, J=7.3 Hz), 5.45 (2H, s), 7.23–7.36 (2H, m), 7.58–7.75 (2H, m), 7.88 (1H, s); MS (ES$^+$) m/e 422 [MH]$^+$. Anal. Found C, 62.56; H, 5.67; N, 23.18%. C$_{22}$H$_{24}$FN$_7$O requires C, 62.69; H, 5.74; N, 23.26%.

EXAMPLE 4

3-Cyclopentyl-7-(2-fluorophenyl)-4-methyl-2-(2-methyl-2H-[1,2,4]triazol-3-ylmethoxy)pyrazolo[1,5-d][1,2,4]triazine To toluene-4-sulfonic acid 3-cyclopentyl-7-(2-fluorophenyl)-4-methylpyrazolo[1,5-d][1,2,4]triazin-2-yl ester (Example 3, step c; 230 mg, 0.494 mmol) and (2-methyl-2H-[1,2,4]triazol-3-yl)methanol (67 mg, 1.2 molar eq; prepared as described in EP-A-170073) in DMF (10 ml) was added sodium hydride (22 mg of a 60% dispersion in mineral oil; 1.2 molar eq) and the mixture was stirred at room temperature for 1 h. Water (90 ml) was added then the solution was extracted with diethyl ether (4×50 ml). The combined ether layers were washed with brine (1×100 ml), dried (Na$_2$SO$_4$), the solvent was removed in vacuo and the residue was purified by flash chromatography on silica gel eluting with 0 to 50% ethyl acetate in dichloromethane. 3-Cyclopentyl-7-(2-fluorophenyl)-4-methyl-2-(2-methyl-2H-[1,2,4]triazol-3-ylmethoxy)pyrazolo[1,5-d][1,2,4]triazine was isolated as a gum, which solidified upon trituration under diethyl ether/isohexane (77 mg, mp=123° C.). $^1$H NMR (360 MHz, CDCl$_3$) δ 1.60–1.98 (8H, m), 2.88 (3H, s), 3.42 (1H, m), 3.73 (3H, s), 5.44 (2H, s), 7.22–7.37 (2H, m), 7.56–7.71 (2H, m), 7.85 (1H, s); MS (ES$^+$) m/e 408 [MH]$^+$. Anal. Found C, 61.64; H, 5.31; N, 23.77%. $C_{21}H_{22}FN_7O$ requires C, 61.90; H, 5.44; N, 24.06%.

EXAMPLE 5

3-Cyclopentyl-2-(2-ethyl-2H-[1,2,4]triazol-3-ylmethoxy)-4-methyl-7-phenyl-pyrazolo[1,5-d][1,2,4]triazine a) Toluene-4-sulfonic acid 3-cyclopentyl-4-methyl-7-phenylpyrazolo[1,5-d][1,2,4]triazine-2-yl ester Toluene-4-sulfonic acid 5-acetyl-4-cyclopentyl-1H-pyrazol-3-yl ester (0.65 g, 1.87 mmol) and benzhydrazide (0.28 g, 1.1 molar eq) were stirred together in xylene (20 ml) at reflux for 2.5 h. The solvent was reduced to ~5 ml and Dowtherm A (20 ml) was added and the reaction mixture was heated at 180° C. for 2 h. The mixture was cooled and poured directly onto a column of silica gel, and the Dowtherm was eluted off with dichloromethane before eluting the product off with 3–6% ethyl acetate in dichloromethane (UV detection). Toluene-4-sulfonic acid 3-cyclopentyl-4-methyl-7-phenylpyrazolo[1,5-d][1,2,4]triazin-2-yl ester was obtained as a light brown solid (0.62 g). $^1$H NMR (360 MHz, CDCl$_3$) δ 1.73–2.07 (8H, m), 2.49 (3H, s), 2.91 (3H, s), 3.48 (1H, m), 7.26–7.61 (5H, m), 7.93–7.97 (2H, m), 8.13–8.15 (2H, d, J=8.7 Hz); MS (ES$^+$) m/e 449 [MH]$^+$.

b) 3-Cyclopentyl-2-(2-ethyl-2H-[1,2,4]triazol-3-ylmethoxy)-4-methyl-7-phenylpyrazolo[1,5-d][1,2,4]triazine To toluene-4-sulfonic acid 3-cyclopentyl-4-methyl-7-phenylpyrazolo[1,5-d][1,2,4]triazin-2-yl ester (300 mg, 0.67 mmol) and (2-ethyl-2H-[1,2,4]triazol-3-yl)methanol (102 mg, 1.2 molar eq; prepared as described in EP-A-170073) in DMF (10 ml) was added sodium hydride (29.5 mg of a 60% dispersion in mineral oil; 1.2 molar eq) and the mixture was stirred at room temperature for 1 h. Water (90 ml) was added then the solution was extracted with diethyl ether (4×60 ml). The combined ether layers were washed with brine (1×100 ml), dried (Na$_2$SO$_4$), the solvent was removed in vacuo and the residue was purified by flash chromatography on silica gel eluting with 0 to 50% ethyl acetate in dichloromethane. 3-Cyclopentyl-2-(2-ethyl-2H-[1,2,4]triazol-3-ylmethoxy)-4-methyl-7-phenylpyrazolo[1,5-d][1,2,4]triazine was isolated as a gum, which solidified upon trituration under diethyl ether/isohexane (144 mg, mp=112° C.). $^1$H NMR (360 MHz, CDCl$_3$) δ 1.42 (3H, t, J=7.3 Hz), 1.66–1.95 (8H, m), 2.87 (3H, s), 3.43 (1H, m), 4.20 (2H, q, J=7.3 Hz), 5.55 (2H, s), 7.51–7.61 (3H, m), 7.93 (1H, s), 8.28–8.31 (2H, m); MS (ES$^+$) m/e 403 [MH]$^+$. Anal. Found C, 65.10; H, 6.06; N, 24.19%. $C_{22}H_{25}N_7O$ requires C, 65.49; H, 6.25; N, 24.06%.

EXAMPLE 6

3-Cyclopentyl-4-methyl-2-(2-methyl-2H-[1,2,4]triazol-3-ylmethoxy)-7-phenylpyrazolo[1,5-d][1,2,4]triazine To toluene-4-sulfonic acid 3-cyclopentyl-4-methyl-7-phenylpyrazolo[1,5-d][1,2,4]triazin-2-yl ester (Example 5, step a; 300 mg, 0.67 mmol) and (2-methyl-2H-[1,2,4]triazol-3-yl)methanol (90.4 mg, 1.2-molar eq; prepared as described in EP-A-170073) in DMF (10 ml) was added sodium hydride (29.5 mg of a 60% dispersion in mineral oil; 1.2 molar eq) and the mixture was stirred at room temperature for 1 h. Water (90 ml) was added then the solution was extracted with diethyl ether (4×50 ml). The combined ether layers were washed with brine (1×100 ml), dried (Na$_2$SO$_4$), the solvent was removed in vacuo and the residue was purified by flash chromatography on silica gel eluting with 0 to 50% ethyl acetate in dichloromethane. 3-Cyclopentyl-4-methyl-2-(2-methyl-2H-[1,2,4]triazol-3-ylmethoxy)-7-phenylpyrazolo[1,5-d][1,2,4]triazine was isolated as a gum, which solidified upon trituration under diethyl ether (152 mg, mp=159° C.). $^1$H NMR (360 MHz, CDCl$_3$) δ 1.66–1.96 (8H, m), 2.86 (3H, s), 3.44 (1H, m), 3.87 (3H, s), 5.54 (2H, s), 7.61–7.58 (3H, m), 7.90 (1H, s), 8.24–8.26 (2H, m); MS (ES$^+$) m/e 389 [MH]$^+$. Anal. Found C, 65.02; H, 5.97; N, 25.31%. $C_{21}H_{23}N_7O$ requires C, 64.76; H, 5.95; N, 25.18%.

EXAMPLE 7

3-tert-Butyl-7-(2,5-difluorophenyl)-2-(2-ethyl-2H-[1,2,4]triazol-3-ylmethoxy)-4-methylpyrazolo[1,5-d][1,2,4]triazine a) 3-tert-Butyl-4-hydroxy-5-methyl-5H-furan-2-one 4-Hydroxy-5-methyl-5H-furan-2-one (15.9 g, 0.14 mol) was dissolved in tert-butanol (13.9 ml, 0.147 mol) with concentrated sulfuric acid (7.8 ml, 0.147 mol) and heated at 40° C. for 4 days. The reaction mixture was allowed to cool and was partitioned between water (75 ml) and diethyl ether (75 ml). The organic layer was separated and dried (Na$_2$SO$_4$), filtered and concentrated under vacuum. Chromatography on silica gel with diethyl ether as eluent gave a crude product which was further purified by chromatography on silica gel with dichloromethane as eluent then triturated with diethyl ether to give 3-tert-butyl-4-hydroxy-5-methyl-5H-furan-2-one (3.1 g) as a white solid. $^1$H NMR (360 MHz, CDCl$_3$) δ 1.34 (9H, s), 1.46 (3H, d, J=6.7 Hz), 4.69 (1H, q, J=6.7 Hz).

b) 4-tert-Butyl-5-(1-hydroxyethyl-3-(4-methylphenyl)sulfonyloxypyrazole 3-tert-Butyl-4-hydroxy-5-methyl-5H-furan-2-one (3 g, 17.7 mmol) was dissolved in ethanol (40 ml) with hydrazine hydrate (2.73 ml, 88.5 mmol) and heated under reflux for 14 h. The volume was reduced by evaporation to ~15 ml and heating continued for a further 48 h. The solvents were removed under high vacuum and the residue was triturated with diethyl ether to leave a white solid (crude 4-tert-butyl-5-(1-hydroxyethyl)pyrazol-3-one, 2.6 g). This white solid (2.6 g, 14 mmol) was dissolved in dichloromethane (70 ml) with tosyl chloride (3.24 g, 16.8 mmol) then cooled to 0° C. and triethylamine (2.56 ml, 18.2 mmol) was added dropwise. The reaction mixture was allowed to warm to ambient temperature then diluted with more dichloromethane (50 ml) and washed with saturated brine (1×100 ml). The organic layer was dried (Na$_2$SO$_4$), filtered and concentrated under vacuum to leave a residue which was purified on silica gel using 20–50% ethyl acetate in isohexane as eluent to give 4-tert-butyl-5-(1-hydroxyethyl)-3-(4-methylphenyl)sulfonyloxypyrazole (3.8 g) as a white solid. $^1$H NMR (360 MHz, CDCl$_3$) δ 1.34 (9H, s), 1.50 (3H, d, J=6.7 Hz), 2.45 (3H, s), 5.26 (1H, q, J=6.7 Hz), 7.35 (2H, d, J=8.2 Hz), 7.95 (2H, d, J=8.2 Hz), 10.72 (1H, br s); MS (ES$^+$) m/e 339 [MH]$^+$.

c) 5-Acetyl-4-tert-butyl-3-(4-methylphenyl)sulfonyloxypyrazole 4-tert-Butyl-5-(1-hydroxyethyl)-3-(4-methylphenyl)sulfonyloxypyrazole (3.8 g, 11.3 mmol) was dissolved in dichloromethane (100 ml) and PDC (4.26 g, 11.3 mmol) was added After stirring at ambient temperature for 2 h, the reaction mixture was poured directly onto a silica gel column and eluted with dichloromethane then 20% ethyl acetate/dichloromethane to give the required product (2.71 g) as a white solid. $^1$H NMR (360 MHz, CDCl$_3$) δ 1.26 (9H, s), 2.46 (3H, s), 2.56 (3H, s), 7.36 (2H, d, J=8.2 Hz), 7.82 (2H, d, J=8.2 Hz), 10.70 (1H, br s); MS (ES$^+$) m/e 337 [MH]$^+$.

d) Toluene-4-sulfonic acid 3-tert-butyl-7-(2,5-difluorophenyl)-4-methylpyrazolo[1,5-d][1,2,4]triazin-2-yl ester 5-Acetyl-4-tert-butyl-3-(4-methylphenyl)sulfonyloxypyrazole (0.4 g, 1.19 mmol) was dissolved in xylene (20 ml) with 2,5-difluorobenzoic hydrazide (0.225 g, 1.31 mmol) and heated under reflux for 14 h. The xylene was removed by evaporation and replaced with Dowtherm A (15 ml) and heated at 180° C. for 4 h. The reaction mixture was allowed to cool to room temperature and poured directly onto a silica column and eluted with dichloromethane then 1–5% ethyl acetate/dichloromethane to give the required product (0.3 g) as a white solid. $^1$H NMR (360 MHz, CDCl$_3$) δ 1.64 (9H, s), 2.42 (3H, s), 3.11 (3H, s), 7.11–7.83 (8H, m); MS (ES$^+$) m/e 473 [MH]$^+$.

e) 3-tert-Butyl-7-(2,5-difluorophenyl)-4-methyl-2-(2-methyl-2H-[1,2,4]triazol-3-ylmethoxy)pyrazolo[1,5-d][1,2,4]triazine To toluene-4-sulfonic acid 3-tert-butyl-7-(2,5-difluorophenyl)-4-methylpyrazolo[1,5-d][1,2,4]triazin-2-yl ester (0.3 g, 0.636 mmol) and (2-ethyl-2H-[1,2,4]triazol-3-yl)methanol (97.3 mg, 1.2 molar eq; prepared as described in EP-A-170073) in DMF (10 ml) was added sodium hydride (30 mg of a 60% dispersion in mineral oil; 1.2 molar eq) and the mixture was stirred at room temperature for 1 h. Water (150 ml) was added then the solution was extracted with diethyl ether (4×50 ml). The combined ether layers were washed with brine (1×100 ml), dried (Na$_2$SO$_4$), the solvent was removed in vacuo and the residue was purified by flash chromatography on silica gel eluting with 0 to 50% ethyl acetate in dichloromethane. 3-tert-Butyl-7-(2,5-difluorophenyl)-2-(2-ethyl-2H-[1,2,4]triazol-3-ylmethoxy)-4-methylpyrazolo[1,5-d][1,2,4]triazine was isolated as a gum, which solidified upon trituration under diethyl ether/isohexane (10 mg, mp=109° C.). $^1$H NMR (360 MHz, CDCl$_3$) δ 1.40 (3H, t, J=7.3 Hz), 1.55 (9H, s), 3.08 (3H, s), 4.14 (2H, q, J=7.3 Hz), 5.48 (2H, s), 7.18–7.41 (3H, m), 7.88 (1H, s); MS (ES$^+$) m/e 428 [MH]$^+$.

EXAMPLE 8

3-tert-Butyl-4-methyl-2-(2-methyl-2H-[1,2,4]triazol-3-ylmethoxy)-7-(2,3,6-trifluorophenyl)pyrazolo[1,5-d][1,2,4]triazine a) 2,3,6-Trifluorobenzoic hydrazide To 2,3,6-trifluorobenzoyl chloride (29 g, 0.15 mol) in dichloromethane (200 ml) was added methanol (30 ml) dropwise at 5° C. The solution was allowed to warm to room temperature and was stirred under nitrogen for 2 h. The solvent was removed in vacuo and the residual oil was stirred with hydrazine monohydrate (19 ml, 0.40 mol) in ethanol (120 ml) at reflux for 3 h. The solvent was removed in vacuo, and the residue was partitioned between dichloromethane (400 ml) and water (200 ml). The biphasic mixture was filtered to remove insoluble material, then the aqueous layer was washed with dichloromethane (2×300 ml). The combined organic layers were dried over magnesium sulfate, and were concentrated in vacuo to yield 2,3,6-trifluorobenzoic hydrazide as a white solid (6.0 g).

Data for the title compound: $^1$H NMR (400 MHz, CDCl$_3$) δ 4.18 (2H, br s), 6.93 (1H, m), 7.25 (2H, m); MS (ES$^+$) m/e 191 [MH]$^+$.

b) Toluene-4-sulfonic acid 3-tert-butyl-4-methyl-7-(2,3,6-trifluorophenyl)pyrazolo[1,5-d][1,2,4]triazin-2-yl ester This compound was prepared using the procedure described in Example 7, step d, using 2,3,6-trifluorobenzoic hydrazide instead of 2,5-difluorobenzoic hydrazide. Data for the title compound: $^1$H NMR (360 MHz, CDCl$_3$) δ 1.65 (9H, s), 2.42 (3H, s), 3.13 (3H, s), 6.98 (1H, m), 7.21 (2H, d, J=8.2 Hz), 7.38 (1H, m), 7.74 (2H, d, J=8.4 Hz); MS (ES$^+$) m/e 491 [MH]$^+$.

c) 3-tert-Butyl-4-methyl-2-(2-methyl-2H-[1,2,4]triazol-3-ylmethoxy)-7-(2,3,6-trifluorophenyl)pyrazolo[1,5-d][1,2,4]triazine This compound was prepared using the procedure described in Example 7, step e, using (2-methyl-2H-[1,2,4]triazol-3-yl)methanol (prepared as described in EP-A-170073) instead of (2-ethyl-2H-[1,2,4]triazol-3-yl)methanol, and using toluene-4-sulfonic acid 3-tert-butyl-4-methyl-7-(2,3,6-trifluorophenyl)pyrazolo[1,5-d][1,2,4]triazin-2-yl ester instead of toluene-4-sulfonic acid 3-tert-butyl-7-(2,5-difluorophenyl)-4-methylpyrazolo[1,5-d][1,2,4]triazin-2-yl ester. Data for the title compound: $^1$H NMR (400 MHz, CDCl$_3$) δ 1.55 (9H, s), 3.07 (3H, s), 3.84 (3H, s), 5.38 (2H, s), 7.04 (1H, m), 7.41 (1H, m), 7.86 (1H, s); MS (ES$^+$) m/e 432 [MH]$^+$.

EXAMPLE 9

3-(2-Fluorophenyl)-methyl-2-(2-methyl-2H-[1,2,4]triazol-3-ylmethoxy)-7-(pyrazin-2-yl)pyrazolo[1,5-d][1,2,4]triazine a) Toluene-4-sulfonic acid 3-(2-fluorophenyl)-4-methyl-7-(pyrazin-2-yl)pyrazolo[1,5-d][1,2,4]triazin-2-yl-ester This compound was prepared using the procedure described in Example 1, step d, using pyrazine carbohydrazide instead of 2-fluorobenzhydrazide. Data for the title compound: $^1$H NMR (400 MHz, CDCl$_3$) δ 2.46 (3H, s), 2.56 (3H, s), 7.20 (1H, t, J=9.2 Hz), 7.40 (3H, m), 7.42 (1H, td, J=7.4, 1.7 Hz), 7.49 (1H, m), 7.78 (2H, d, J=8.3 Hz); MS (ES$^+$) m/e 477 [MH]$^+$.

b) 3-(2-Fluorophenyl-4-methyl-2-(2-methyl-2H-[1,2,4]triazol-3-ylmethoxy)-7-(pyrazin-2-yl)pyrazolo[1,5-d][1,2,4]triazine This compound was prepared using the procedure described in example 7, step e, using (2-methyl-2H-[1,2,4]triazol-3-yl)methanol (prepared as described in EP-A-170073) instead of (2-ethyl-2H-[1,2,4]triazol-3-yl)methanol, and using toluene-4-sulfonic acid 3-(2-fluorophenyl)-4-methyl-7-(pyrazin-2-yl)pyrazolo[1,5-d][1,2,4]triazin-2-yl ester instead of toluene-4-sulfonic acid 3-tert-butyl-7-(2,6-difluorophenyl)-4-methylpyrazolo[1,5-d][1,2,4]triazin-2-yl ester. Data for the title compound: $^1$H NMR (400 MHz, CDCl$_3$) δ 2.54 (3H, s), 3.84 (3H, s), 5.54 (1H, d, J=13 Hz), 5.58 (1H, d, J=13 Hz), 7.21 (1H, m), 7.26 (1H, m), 7.36 (1H, td, J=7.4, 1.8 Hz), 7.46 (1H, m), 7.84 (1H, s), 8.85 (2H, m), 9.48 (1H, d, J=1.4 Hz); MS (ES$^+$) m/e 418 [MH]$^+$. Anal. Found C, 57.37; H, 3.73; N, 28.99%. C$_{20}$H$_{16}$FN$_9$O.0.3 H$_2$O.0.07 C$_6$H$_{14}$ requires C, 57.19; H, 4.13; N, 29.40%.

EXAMPLE 10

3,7-Bis(2-fluorophenyl-4-methyl-2-(1-methyl-1H-[1,2,4]triazol-3-ylmethoxy)pyrazolo[1,5-d][1,2,4]triazine This compound was prepared using the procedure described in Example 1, step e, using (1-methyl-1H-[1,2,4]- triazol-3yl)methanol (prepared as described in WO 98/04559) instead of (2-methyl-2H-[1,2,4]triazol-3-yl) methanol. Data for the title compound: $^1$H NMR (400 MHz, CDCl$_3$) δ 2.51 (3H, s), 3.88 (3H, s), 5.37 (1H, d, J=12 Hz), 5.45 (1H, d, J=12 Hz), 7.15–7.28 (3H, m), 7.33–7.40 (3H, m), 7.44 (1H, td, J=7.4, 1.7 Hz), 7.69 (1H, m), 7.82 (1H, m), 7.97 (1H, 8); MS (ES$^+$) m/e 434 [MH]$^+$.

EXAMPLE 11

2-(2-Ethyl-2H-[1,2,4]triazol-3-ylmethoxy)-3-(2-fluorophenyl)-4-methyl-7-(thien-3-yl)pyrazolo[1,5-d][1,2,4]triazine a) Toluene-4-sulfonic acid 3-(2-fluorophenyl)-4-methyl-7-(thien-3-yl)pyrazolo[1,5-d][1,2,4]triazin-2-yl ester This compound was prepared using the procedure described in Example 1, step d, using thiophene-3-carbohydrazide instead of 2-fluorobenzhydrazide. Data for the title compound: $^1$H NMR (400 MHz, CDCl$_3$) δ 2.50 (3H, s), 2.51 (3H, 6), 7.19 (1H, m), 7.29 (1H, td, J=7.5, 0.8 Hz), 7.33 (2H, d, J=8.2 Hz), 7.41–7.52 (3H, m), 7.81 (211, d, J=8.3 Hz), 8.16 (1H, dd, J=5.1, 1.1 Hz), 8.57 (1H, dd, J=3.0, 1.1 Hz); MS (ES$^+$) m/e 481 [MH]$^+$.

b) 2-(2-Ethyl-2H-[1,2,4]triazol-3-ylmethoxy)-3-(2-fluorophenyl)-4-methyl-7-(thien-3-yl)pyrazolo[1,5-d][1,2,4]triazine This compound was prepared as described in Example 7, step e, using toluene-4-sulfonic acid 3-(2-fluorophenyl)-4-methyl-7-(thien-3-yl)pyrazolo[1,5-d][1,2,4]triazin-2-yl ester instead of toluene-4-sulfonic acid 3-tert-butyl-7-(2,5-difluorophenyl)-4-methylpyrazolo[1,5-d][1,2,4]triazin-2-yl ester. Data for the title compound: $^1$H NM (400 MHz, CDCl$_3$) δ 1.32 (3H, t, J=7.2 Hz), 2.48 (3H, s), 4.21 (2H, q, J=7.2 Hz), 5.67 (1H, d, J=13 Hz), 5.72 (1H, d, J=13 Hz), 7.18–7.27 (2H, m), 7.36 (1H, td, J=7.4, 1.7 Hz), 7.42–7.49 (2H, m), 7.90 (1H, s), 8.28 (1H, dd, J=5.2, 1.2 Hz), 9.16 (1H, m); MS (ES$^+$) m/e 436 [MH]$^+$. Anal Found C, 58.01; H, 4.05; N, 22.32%. C$_{21}$H$_{18}$FN$_7$OS requires C, 67.92; H, 4.17; N, 22.51%.

EXAMPLE 12

3-(2-Fluorophenyl)-4-methyl-2-(1-methyl-1H-[1,2,4]triazol-3-ylmethoxy)-7-thien-3-yl)pyrazolo[1,5-d][1,2,4]triazine This compound was prepared using the procedure described in Example 11, step b, using (1-methyl-1H-[1,2,4]triazol-3-yl)methanol (prepared as described in WO 98/04559) instead of (2-ethyl-2H-[1,2,4]triazol-3-yl) methanol. Data for the title compound: $^1$H NMR (400 MHz, CDCl$_3$) δ 2.48 (3H, s), 3.92 (3H, s), 5.56 (1H, d, J=12 Hz), 5.63 (1H, d, J=12 Hz), 7.16–7.26 (2H, m), 7.38–7.47 (3H, m), 8.01 (1H, s), 8.30 (1H, dd, J=5.2, 1.1 Hz), 9.27 (1H, dd, J=3.0, 1.1 Hz); MS (ES$^+$) m/e 422 [MH]$^+$. Anal. Found C, 56.87; H, 3.67; N, 22.99%. C$_{20}$H$_{16}$FN$_7$OS requires C, 57.00; H, 3.83; N, 23.26%.

EXAMPLE 13

3-Cyclohexyl-7-(2-fluorophenyl)-4-methyl-2-(2-methyl-2H-[1,2,4]triazol-3-ylmethoxy)pyrazolo[1,5-d][1,2,4]triazine This compound was prepared using the procedure described in Example 3, steps a, b, c and d, using 2-bromo-2-cyclohexylacetyl chloride in step a instead of 2-bromo-2-cyclopentylacetyl chloride, and using (2-methyl-2H-[1,2,4]triazol-3-yl)methanol prepared as described in EP-A-170073) instead of (2-ethyl-2H-[1,2,4]triazol-3-yl)methanol in step d. Data for the title compound: $^1$H NMR (400 MHz, CDCl$_3$) δ 1.26–1.38 (3H, m), 1.74–1.86 (7H, m), 2.87 (3H, s), 3.02 (1H, m), 3.75 (3H, s), 5.43 (2H, s), 7.24 (1H, m), 7.34 (1H, td, J=7.6, 0.9 Hz), 7.58 (1H, m), 7.69 (1H, m), 7.85 (1H, s); MS (ES$^+$) m/e 422 [MH]$^+$. Anal. Found C, 62.89; H, 5.68; N, 23.13%. C$_{22}$H$_{24}$FN$_7$O requires C, 62.29; H, 5.74; N, 23.26%.

EXAMPLE 14

7-(2-Fluorophenyl)-4-methyl-2-(2-methyl-2H-[1,2,4]triazol-3-ylmethoxy)-3-(thien-3-yl)pyrazolo[1,5-d][1,2,4]triazine a) (S)-3-Hydroxy-5-(1-hydroxyethyl)-1H-pyrazole To a stirred solution of (S)-5-methyltetronic acid (prepared as described by Brandange et al., *J. Org. Chem.*, 1984, 49, 927) (12.32 g, 0.108 mmol) in ethanol (85 ml) was added hydrazine hydrate (6.29 ml, 0.130 mmol) and the mixture was heated at reflux for 5 h. The solvents were removed in vacuo and the residue was recrystallised from ethanol-ethyl acetate (1:1) to afford 10.49 g (76%) of the title compound: $^1$H NMR (360 MHz, DMSO-d$_6$) δ 1.31 (3H, d, J=6.5 Hz), 4.60 (1H, m), 5.11 (1H, d, J 4.8 Hz), 5.30 (1H, s).

b) Toluene-4-sulfonic acid 5-[(S)-1-hydroxyethyl]-1H-pyrazol-3-yl ester

To a stirred solution of (S)-3-hydroxy-5-(1-hydroxyethyl)-1H-pyrazole (0.5056 g, 3.95 mmol) in anhydrous dichloromethane (20 ml) under nitrogen was added p-toluenesulfonyl chloride (0.8276 g, 4.34 mmol) then, dropwise, triethylamine (0.66 ml, 4.74 mmol). The mixture was stirred at room temperature for 3 h, then washed with saturated NaCl (15 ml). The aqueous layer was further extracted with dichloromethane (2×25 ml) and the combined organic extracts were dried (NaSO$_4$) and evaporated in vacuo. The residue was purified by flash chromatography (silica gel, 5% MeOH/CH$_2$Cl$_2$) to give 0.8770 g (79%) of the title compound as an orange oil: $^1$H NMR (400 MHz, DMSO-d$_6$) δ 1.31 (3H, d, J=6.5 Hz), 2.42 (3H, s), 4.67 (1H, m), 5.40 (1H, d, J=5.1 Hz), 5.79 (1H, d, J=2.1 Hz), 7.47 (2H, d, J=8.1 Hz), 7.77 (2H, d, J=8.4 Hz), 12.48 (1H, s); MS (ES$^+$) m/e 283 [M+H]$^+$, 265 [M–OH]$^+$.

c) Toluene-4-sulfonic acid 5-acetyl-1H-pyrazol-3-yl ester

To toluene-4-sulfonic acid 5-[(S)-1-hydroxyethyl]-1H-pyrazol-3-yl ester (6.09 g, 21.6 mmol) in anhydrous dichloromethane (180 ml) was added pyridinium dichromate (9.74 g, 25.9 mmol) and the resulting slurry was stirred at room temperature for 17.6 h. The mixture was poured directly onto a column of silica gel, which was eluted with ethyl acetate to yield 5.13 g (85%) of the title compound as a whitish solid: $^1$H NMR (360 MHz, DMSO-d$_6$) δ 2.43 (3H, s), 2.45 (3H, s), 6.78 (1H, s), 7.49 (2H, d, J=8.2 Hz), 7.80 (2H, d, J=8.3 Hz), 13.72 (1H, s); MS (ES$^+$) m/e 281 [M+H]$^+$.

d) Toluene-4-sulfonic acid 7-(2-fluorophenyl)-4-methylpyrazolo[1,5-d][1,2,4]triazin-2-yl ester A mixture of toluene-4-sulfonic acid 5-acetyl-1H-pyrazol-3-yl ester (2.52 g, 8.99 mmol) and 2-fluorobenzhydrazide (1.53 g, 9.90 mmol) in xylene (110 ml) was heated at reflux for 17 h under nitrogen. The solvent was removed in vacuo, and the residue was heated in Dowtherm A at 180° C. for 18 h The mixture was poured directly onto a column of silica gel, which was eluted with dichloromethane, then 25% EtOAc/CH$_2$Cl$_2$, to give 3.40 g (95%) of the title compound as a brown solid: $^1$H NMR (360 MHz, CDCl$_3$) δ 2.45 (3H, s), 2.83 (3H, s), 6.71 (1H, s), 7.18 (1H, t, J=9.5 Hz), 7.30 (2H, d, J=7.8 Hz), 7.31 (1H, m), 7.59 (1H, m), 7.66 (1H, m), 7.82 (2H, d, J=8.4 Hz); MS (ES$^+$) m/e 399 [M+H]$^+$.

e) 7-(2-Fluorophenyl)-2-hydroxy-4-methylpyrazolo[1,5-d][1,2,4]triazine

To a stirred solution of toluene-4-sulfonic acid 7-(2-fluorophenyl)-4-methylpyrazolo[1,5-d][1,2,4]triazin-2-yl ester (3.39 g, 8.51 mmol) in 1,4-dioxane (150 ml) and water (30 ml) was added 4 N aqueous NaOH (10.64 ml, 42.6 mmol) and the mixture was stirred at room temperature for 4 h. The mixture was concentrated in vacuo to about 30 ml, and the aqueous residue was diluted with water (150 ml) and washed with ethyl acetate (50 ml). The remaining aqueous layer was acidified to pH 5 with 5 N aqueous HCl (4 ml) and the resulting precipitate was collected by filtration, washed with water and dried at 60° C. under vacuum to leave 1.98 g (95%) of the title compound as a cream solid: $^1$H NMR (360 MHz, DMSO-$d_6$) δ 2.68 (3H, s), 6.38 (1H, s), 7.41–7.47 (2H, m), 7.66–7.77 (2H, m); MS (ES$^+$) m/e 245 [M+H]$^+$.

f) 3-Bromo-7-(2-fluorophenyl)-2-hydroxy-4-methylpyrazolo[1,5-d][1,2,4]triazine

To a stirred solution of 7-(2-fluorophenyl)-2-hydroxy-4-methylpyrazolo[1,5-d][1,2,4]triazine (1.48 g, 6.06 mmol) in glacial acetic acid (20 ml) was added, dropwise, bromine (0.343 ml, 6.66 mmol) and the mixture was stirred at room temperature for 20 min. The mixture was then diluted with water (80 ml) and the resulting solid was collected by filtration, washed with water and dried at 60° C. under vacuum to afford 1.85 g (94%) of the title compound as a cream solid: $^1$NMR (360 MHz, DMSO-$d_6$) δ 2.88 (3H, s), 7.42–7.47 (2H, m), 7.67–7.76 (2H, m); MS (ES$^+$) m/e 323/325 [M+H]$^+$.

g) 3-Bromo-7-(2-fluorophenyl)-4-methyl-2-(2-methyl-2H-[1,2,4]triazol-3-ylmethoxy)pyrazolo[1,5-d][1,2,4]triazine To a stirred solution of 3-bromo-7-(2-fluorophenyl)-2-hydroxy-4-methylpyrazolo[1,5-d][1,2,4]triazine (0.5636 g, 1.74 mmol) in anhydrous DMF (28 ml) was added cesium carbonate (2.1927 g, 6.73 mmol) and 5-chloromethyl-1-methyl-1H-[1,2,4]triazole hydrochloride (EP-A-421210) (0.3518 g, 2.09 mmol) and the mixture was stirred at room temperature under nitrogen for 3 days. The mixture was then filtered and the solid washed well with ethyl acetate. The filtrates were diluted to 150 ml with ethyl acetate and washed with saturated aqueous NH$_4$Cl (75 ml). The aqueous layer was further extracted with ethyl acetate (100 ml), and the combined extracts were dried (NaSO$_4$) and evaporated in vacuo. The residue was purified by flash chromatography (silica gel, 2% MeOH/CH$_2$Cl$_2$) to give 0.5367 g (74%) of the title compound as a yellow solid: $^1$H NMR (360 MHz, CDCl$_3$) δ 3.01 (3H, s), 3.85 (3H, s), 5.49 (2H, s), 7.26 (1H, m), 7.37 (1H, td, J=7.6, 0.9 Hz), 7.62 (1H, m), 7.71 (1H, m), 7.86 (1H, s); MS (ES$^+$) m/e 418/420 M+H]$^+$.

h) 7-(2Fluorophenyl)-4-methyl-2-(2-methyl-2H-[1,2,4]triazol-3-ylmethoxy)-3-(thien-3-yl)pyrazolo[1,5-d][1,2,4]triazine A mixture of 3-bromo-7-(2-fluorophenyl)-4-methyl-2-(2-methyl-2H-[1,2,4]triazol-3ylmethoxy)pyrazolo[1,5-d][1,2,4]triazine (100.7 mg, 0.241 mmol), thiophene-3-boronic acid (46.8 mg, 0.366 mmol) and cesium carbonate (157.0 mg, 0.482 mmol) in anhydrous 1,4-dioxane (10 ml) was degassed by three freeze-pump-thaw cycles. Then tris(dibenzylideneacetone)dipalladium(0) (22.5 mg, 0.0246 mmol) and a 0.1M solution of tri-tert-butylphosphine in 1,4-dioxane (0.58 ml, 0.058 mmol) was added and two more freeze-pump-thaw cycles were performed. The mixture was heated at 90° C. under nitrogen for 22 h, then filtered through glass fibre paper. The solid was washed with ethyl acetate, and the filtrates were washed with saturated aqueous NaCl (15 ml). The aqueous layer was further extracted with ethyl acetate (25 ml), and the combined extracts were dried (NaSO$_4$) and evaporated in vacuo. The residue was purified by flash chromatography (silica gel, 2% MeOH/CH$_2$Cl$_2$) to give 83.8 mg (83%) of the title compound as an orange solid: mp=124–129° C. (CH$_2$Cl$_2$-EtOAc-isohexane); $^1$H NMR (360 MHz, CDCl$_3$) δ 2.60 (3H, s), 3.71 (5H, s), 5.46 (2H, s), 7.18 (1H, d, J=4.9 Hz), 7.27 (1H, m), 7.38 (1H, m), 7.38 (1H, s), 7.44 (1H, dd, J=4.9, 3.0 Hz), 7.63 (1H, m), 7.75 (1H, t, J=7.1 Hz), 7.83 (1H, s); MS (ES$^+$) m/e 422 [M+H]$^+$. Anal. Found C, 56.94; H, 4.04; N, 22.49%. C$_{20}$H$_{16}$FN$_7$OS.0.08 C$_4$H$_8$O$_2$ requires C, 56.96; H, 3.91; N, 22.88%.

EXAMPLE 15

7-(2-Florophenyl)-4-methyl-2-(2-methyl-2H-[1,2,4]triazol-3-ylmethoxy-3-phenylpyrazolo[1,5-d][1,2,4]triazine This was prepared in 76% yield using a similar procedure to that described in Example 14, step h, but using phenylboronic acid instead of thiophene-3-boronic acid: mp=150–153° C. (EtOAc-isohexane); $^1$H NMR (360 MHz, CDCl$_3$) δ 2.52 (3H, s), 3.69 (3H, s), 5.46 (2H, 6), 7.28 (1H, m), 7.36–7.48 (6H, m), 7.63 (1H, m), 7.77 (1H, m), 7.82 (1H, s); MS (ES$^+$) m/e 416 [M+H]$^+$. Anal. Found C, 63.32; H, 4.36; N, 23.06%. C$_{22}$H$_{18}$FN$_7$O.0.06 C$_4$H$_8$O$_2$ requires C, 63.49; H, 4.43; N, 23.31%.

EXAMPLE 16

7-(2-Fluorophenyl)-3-(fur-3-yl)-4-methyl-2-(2-methyl-2H-[1,2,4]triazol-3-ylmethoxy)pyrazolo[1,5-d][1,2,4]triazine This was prepared in 76% yield using a similar procedure to that described in Example 14, step h, but using furan-3-boronic acid instead of thiophene-3-boronic acid: mp=150–153° C. (CH$_2$Cl$_2$-EtOAc-isohexane); $^1$H NMR (400 MHz, CDCl$_3$) δ 2.70 (3H, s), 3.73 (3H, s), 5.47 (2H, s), 6.56 (1H, dd J=1.9, 0.8 Hz), 7.27 (1H, m), 7.37 (1H, td, J=7.6, 1.0 Hz), 7.55 (1H, t, J=1.8 Hz), 7.59–7.68 (2H, m), 7.74 (1H, m), 7.84 (1H, s); MS (ES$^+$) m/e 406 [M+H]$^+$. Anal. Found C, 58.33; H, 3.95; N, 23.31%. C$_{20}$H$_{16}$FN$_7$O$_2$.0.07 C$_4$H$_8$O$_2$.0.03 CH$_2$Cl$_2$.0.2 H$_2$O requires C, 58.40; H, 4.11; N, 23.47%.

EXAMPLE 17

7-(2-Fluorophenyl)-4-methyl-2-(1-methyl-1H-[1,2,4]-triazol-3-ylmethoxy)-3-(thien-3-yl)pyrazolo[1,5-d][1,2,4]triazine a) 3-Bromo-7-(2-fluorophenyl)-4-methyl-2-(1-methyl-1H-[1,2,4]triazol-3-ylmethoxy)pyrazolo[1,5-d][1,2,4]triazine This was prepared in 77% yield using a similar procedure to that described in Example 14, step g, but using 3-chloromethyl-1-methyl-1H-[1,2,4]triazole hydrochloride (EP-A-421210) instead of 6-chloromethyl-1-methyl-1H-[1,2,4]triazole hydrochloride and stirring for 7 days instead of 3 days: $^1$H NMR (360 MHz, CDCl$_3$) δ 3.00 (3H, s), 3.93 (3H, s), 5.42 (2H, s), 7.23 (1H, m), 7.33 (1H, td, J=7.5, 0.6 Hz), 7.59 (1H, m), 7.75 (1H, m), 8.03 (1H, s); MS (ES$^+$) m/e 418/420 [M+H]$^+$.

b) 7-(2-Fluorophenyl)-4-methyl-2-(1-methyl-1-H-[1,2,4]triazol-3-ylmethoxy)-3-(thien-3-yl)pyrazol[1,5-d][1,2,4]triazine This was prepared in 64% yield using a similar procedure to that described in Example 14, step h, but using 3-bromo-7-(2-fluorophenyl)-4-methyl-2-(1-methyl-1H-[1,2,4]triazol-3-ylmethoxy)pyrazolo[1,5-d][1,2,4]triazine instead of 3-bromo-7-(2-fluorophenyl)-4-methyl-2-(2-methyl-2H-[1,2,4]triazol-3-ylmethoxy)pyrazolo[1,5-d][1,2,4]triazine: mp=214–217° C. (CH$_2$Cl$_2$-EtOAc-isohexane); $^1$H NMR (400 MHz, CDCl$_3$) δ 2.61 (3H, s), 3.89 (3H, s), 5.41 (2, s), 7.21–7.24 (2H, m), 7.34 (1H, td, J=7.6, 0.8 Hz), 7.37–7.42 (2H, m), 7.59 (1H, m), 7.79 (1H, m), 7.98 (1H, s); MS (ES$^+$) m/e 422 [M+H]$^+$. Anal. Found C, 57.00; H, 3.86; N, 23.22%. C$_{20}$H$_{16}$FN$_7$OS requires C, 57.00; H, 3.83; N, 23.26%.

EXAMPLE 18

7-(2-Fluorophenyl)-4-methyl-2-(1-methyl-1H-[1,2,3triazol-4-ylmethoxy)-3-(thien-3-yl)pyrazolo[1,5-d][1,2,4]triazine a) 4-Chloromethyl-1-methyl-1H-[1,2,3]triazole hydrochloride To thionyl chloride (20 ml) under nitrogen, cooled by an ice bath, was added (1-methyl-1H-[1,2,3]triazol-4-yl)methanol hydrochloride monohydrate (1.996 g, 11.9 mmol). The mixture was stirred for 5 min before removing the cooling bath and heating at reflux for 30 min. The excess thionyl chloride was evaporated in vacuo and the residue was triturated with diethyl ether. The resulting solid was collected by filtration, washed with diethyl ether and dried under vacuum at 60° C. to give the title compound as a white solid: $^1$H NMR (360 MHz, DMSO-d$_6$) δ 4.04 (3H, s), 4.81 (2H, s), 8.13 (1H, s).

b) 3-Bromo-7-(2-fluorophenyl)-4-methyl-2-(1-methyl-1H-[1,2,3]triazol-4-ylmethoxy)pyrazolo[1,5-d][1,2,4]triazine This was prepared in 75% yield using a similar procedure to that described in Example 14, step g, but using 4-chloromethyl-1-methyl-1H-[1,2,3]triazole hydrochloride instead of 5-chloromethyl-1-methyl-1H-[1,2,4]triazole hydrochloride and stirring for 7 days instead of 3 days: $^1$H NMR (360 MHz, CDCl$_3$) δ 3.00 (3H, s), 4.07 (3H, s), 5.48 (2H, s), 7.27 (1H, m), 7.38 (1H, t, J=7.5 Hz), 7.54 (1H, s), 7.63 (1H, m), 7.75 (1H, m); MS (ES$^+$) m/e 418/420 [M+H]$^+$.

c) 7-(2-Fluorophenyl-4-methyl-2-(1-methyl-1H-[1,2,3]triazol-4-ylmethoxy)-3-(thien-3-yl)pyrazolo[1,5-d][1,2,4]triazine This was prepared in 83% yield using a similar procedure to that described in Example 14, step h, but using 3-bromo-7-(2-fluorophenyl)-4-methyl-2-(1-methyl-1H-[1,2,3]triazol-4-ylmethoxy)pyrazolo[1,5-d][1,2,4]triazine instead of 3-bromo-7-(2-fluorophenyl)-4-methyl-2-(2-methyl-2H-[1,2,4]triazol-3-ylmethoxy)pyrazolo[1,5-d][1,2,4]triazine: mp=181–186° C. (EtOAc-isohexane); $^1$H NMR (360 MHz, CDCl$_3$) δ 2.61 (3H, s), 4.04 (3H, s), 5.45 (2H, s), 7.17 (1H, dd, J=4.9, 1.1 Hz), 7.30 (1H, m), 7.35–7.42 (3H, m), 7.47 (1H, s), 7.64 (1H, m), 7.79 (1H, m); MS (ES$^+$) m/e 422 [M+H]$^+$. Anal. Found C, 56.69; H, 3.81; N, 21.33%. C$_{20}$H$_{16}$FN$_7$OS.0.35 C$_4$H$_8$O$_2$ requires C, 56.83; H, 4.19; N. 21.68%.

EXAMPLE 19

7-(4-Fluorophenyl)-4-methyl-2-(2-methyl-2H-[1,2,4]triazol-3-ylmethoxy)-3-(thien-3-yl)pyrazolo[1,5-d][1,2,4]triazine a) Toluene-4-sulfonic acid 7-(4-fluorophenyl)-4-methylpyrazolo[1,5-d]1,2,4]triazin-2-yl ester This was prepared in 97% yield using a similar procedure to that described in Example 14, step d, but using 4-fluorobenzhydrazide instead of 2-fluorobenzhydrazide: $^1$H NMR (360 MHz, CDCl$_3$) δ 2.48 (3H, s), 2.81 (3H, s), 6.68 (1H, s), 7.16 (2H, t, J=8.4 Hz), 7.37 (2H, d, J=8.0 Hz), 7.89 (2H, d, J=8.1 Hz), 8.32 (2H, m); MS (ES$^+$) m/e 399 [M+H]$^+$.

b) 7-(4-Fluorophenyl)-2hydroxy-4-methylpyrazolo[1,5-d][1,2,4]triazine

This was prepared in 98% yield using a similar procedure to that described in Example 14, step e, but using toluene-4-sulfonic acid 7-(4-fluorophenyl)-4-methylpyrazolo[1,5-d][1,2,4]triazin-2-yl ester instead of toluene-4-sulfonic acid 7-(2-fluorophenyl)-4-methylpyrazolo[1,5-d][1,2,4]triazin-2-yl ester: $^1$H NMR (360 MHz, DMSO-d$_6$) δ 2.66 (3H, s), 6.33 (1H, s), 7.43 (2H, t, J=8.9 Hz), 8.39 (2H, dd, J=8.9, 5.6 Hz); MS (ES$^+$) m/e 245 [M+H]$^+$.

c) 3-Bromo-7-(4-fluorophenyl)-2-hydroxy-4-methylpyrazolo[1,5-d][1,2,4]triazine

This was prepared in 98% yield using a similar procedure to that described in Example 14, step f, but using 7-(4-fluorophenyl)-2-hydroxy-4-methylpyrazolo[1,5-d][1,2,4]triazine instead of 7-(2-fluorophenyl)-2-hydroxy-4-methylpyrazolo[1,5-d][1,2,4]triazine: $^1$H NMR (400 MHz, DMSO-d$_6$) δ 2.87 (3H, s), 7.45 (2H, t, J=8.9 Hz), 8.26 (2H, dd, J=8.9 and 5.6 Hz); MS (ES$^+$) m/e 323/325 [M+H]$^+$.

d) 3-Bromo-7-(4-fluorophenyl)-4-methyl-2-(2-methyl-2H-[1,2,4]triazol-3-ylmethoxy)pyrazolo[1,5-d][1,2,4]triazine This was prepared in 69% yield using a similar procedure to that described in Example 14, step g, but using 3-bromo-7-(4-fluorophenyl)-2-hydroxy-4-methylpyrazolo[1,5-d][1,2,4]triazine instead of 3-bromo-7-(2-fluorophenyl)-2-hydroxy-4-methylpyrazolo[1,5-d][1,2,4]triazine and stirring for 1 day instead of 3 days: $^1$H NMR (360 MHz, CDCl$_3$) δ 3.00 (3H, s), 4.00 (3H, s), 5.62 (2H, s), 7.26 (2H, t, J=8.7 Hz), 7.91 (1H, s), 8.38 (2H, dd, J=9.0, 5.4 Hz); MS (ES$^+$) m/e 418/420 [M+H]$^+$.

e) 7-(4-Fluorophenyl)-4-methyl-2-(2-methyl-2H-[1,2,4]triazol-3-ylmethoxy)-3-(thien-3-yl)pyrazolo[1,6-d][1,2,4]triazine This was prepared in 76% yield using a similar procedure to that described in Example 14, step h, but using 3-bromo-7-(4-fluorophenyl)-4-methyl-2-(2-methyl-2H-[1,2,4]triazol-3-ylmethoxy)pyrazolo[1,5-d][1,2,4]triazine instead of 3-bromo-7-(2-fluorophenyl)-4-methyl-2-(2-methyl-2H-[1,2,4]triazol-3-ylmethoxy)pyrazolo[1,5-d][1,2,4]triazine: mp=171–177° C. (CH$_2$Cl$_2$-EtOAc-isohexane); $^1$H NMR (400 MHz, CDCl$_3$) δ 2.56 (3H, s), 3.84 (3H, s), 5.59 (2H, s), 7.16 (1H, dd, J=5.0, 1.2 Hz), 7.27 (2H, t, J=8.8 Hz), 7.36 (1H, dd, J=3.0, 1.2 Hz), 7.45 (1H, dd, J=5.0, 3.0 Hz), 7.88 (1H, s), 7.75 (2H, dd, J=9.0, 5.4 Hz); MS (ES$^+$) $^{m/e}$ 422 [M+H]$^+$. Anal. Found C, 56.30; H, 3.52; N, 22.83%. C$_{20}$H$_{16}$FN$_7$OS.0.3 H$_2$O requires C, 56.28; H, 3.92; N, 22.97%.

EXAMPLE 20

7-(2,4-Difluorophenyl)-4-methyl-2-(2-methyl-2H-[1,2,4]triazol-3-ylmethoxy)-3-(thien-3-yl)pyrazolo[1,5-d][1,2,4]triazine a) Toluene-4-sulfonic acid 7-(2,4-difluorophenyl)-4-methylpyrazolo[1,5-d][1,2,4]triazin-2-yl ester This was prepared in 87% yield using a similar procedure to that described in Example 14, step d, but using 2,4-difluorobenzhydrazide instead of 2-fluorobenzhydrazide: $^1$H NMR (360 MHz, CDCl$_3$) δ 2.46 (3H, s), 2.83 (3H, s), 6.71 (1H, s), 6.93 (1H, td, J=7.4, 2.7 Hz), 7.05 (1H, m), 7.31 (2H, d, J=8.1 Hz), 7.68 (1H, m), 7.82 (2H, d, J=8.3 Hz); MS (ES$^+$) m/e 417 [M+M]$^+$.

b) 7-(2,4-Difluorophenyl)-2-hydroxy-4-methylpyrazolo[1,5-d][1,2,4]triazine

This was prepared in 92% yield using a similar procedure to that described in Example 14, step e, but using toluene-4-sulfonic acid 7-(2,4-difluorophenyl)-4-methylpyrazolo[1,5-d][1,2,4]triazin-2-yl ester instead of toluene-4-sulfonic acid 7-(2-fluorophenyl)-4-methylpyrazolo[1,5-d][1,2,4]triazin-2-yl ester: $^1$H NMR (400 MHz, DMSO-$d_6$) δ 2.50 (3H, s), 6.36 (1H, s), 7.30 (1H, m), 7.52 (1H, m), 7.84 (1H, td, J=8.36, 6.52 Hz); MS (ES$^+$) m/e 263 [M+H]$^+$.

c) 3-Bromo-7-(2,4-difluorophenyl)-2-hydroxy-4-methylpyrazolo[1,5-d][1,2,4]triazine This was prepared in 93% yield using a similar procedure to that described in Example 14, step f, but using 7-(2,4-difluorophenyl)-2-hydroxy-4-methylpyrazolo[1,5-d][1,2,4]triazine instead of 7-(2-fluorophenyl)-2-hydroxy-4-methylpyrazolo[1,5-d][1,2,4]triazine: $^1$H NMR (360 MHz, DMSO-$d_6$) δ 2.88 (3H, s), 7.34 (1H, td, J=8.6, 2.3 Hz), 7.54 (1H, td, J=9.3, 2.4 Hz), 7.83 (1H, td, J=8.31, 6.4 Hz); MS (ES$^+$) m/e 340/342 [M+H]$^+$.

d) 3-Bromo-7-(2,4-difluorophenyl)-4-methyl-2-(2-methyl-2H-[1,2,4]triazol-3-ylmethoxy)pyrazolo[1,5-d][1,2,4]triazine This was prepared in 72% yield using a similar procedure to that described in Example 14, step g, but using 3-bromo-7-(2,4-difluorophenyl)-2-hydroxy-4-methylpyrazolo[1,5-d][1,2,4]triazine instead of 3-bromo-7-(2-fluorophenyl)-2-hydroxy-4-methylpyrazolo[1,5-d][1,2,4]triazine and stirring for 21 h instead of 3 days: $^1$H NMR (360 MHz, CDCl$_3$) δ 3.01 (3H, s), 3.93 (3H, s), 5.50 (2H, s), 7.01 (1H, m), 7.10 (1H, m), 7.72 (1H, m), 7.87 (1H, s); MS (ES$^+$) m/e 436/438 [M+H]$^+$.

e) 7-(2,4-Difluorophenyl)-4-methyl-2-(2-methyl-2H-[1,2,4]triazol-3-ylmethoxy)-3-(thien-3-yl)pyrazolo[1,5-d][1,2,4]triazine This was prepared in 36% yield using a similar procedure to that described in Example 14, step h, but using 3-bromo-7-(2,4-difluorophenyl)-4-methyl-2-(2-methyl-2H-[1,2,4]triazol-3-ylmethoxy)pyrazolo[1,5-d][1,2,4]triazine instead of 3-bromo-7-(2-fluorophenyl)-4-methyl-2-(2-methyl-2H-[1,2,4]triazol-3-ylmethoxy)pyrazolo[1,5-d][1,2,4]triazine: mp=144–146° C. (CH$_2$Cl$_2$-EtOAc-isohexane); $^1$H NMR (400 MHz, CDCl$_3$) δ 2.59 (3H, s), 3.76 (3H, s), 5.48 (2H, s), 7.01 (1H, t, J=1.2 Hz), 7.11 (1H, d, J=2.4 Hz), 7.16 (1H, dd, J=5.0, 1.2 Hz), 7.37 (1H, dd, J=3.0, 1.2 Hz), 7.44 (1H, dd, J=5.0, 3.0 Hz), 7.76 (2H, m), 7.83 (1H, s); MS (ES$^+$) m/e 440 [M+H]$^+$.

What is claimed is:

1. A compound of formula I, or a pharmaceutically acceptable salt thereof:

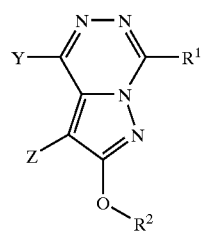

(I)

wherein

Y represents $C_{1-6}$ alkyl;

Z represents halogen; or $C_{1-6}$ alkyl, $C_{3-7}$ cycloalkyl, $C_{4-7}$ cycloalkenyl, $C_{6-8}$ bicycloalkyl, aryl, $C_{3-7}$ heterocycloalkyl, heteroaryl or di($C_{1-6}$)alkylamino, any of which groups may be optionally substituted;

R$^1$ represents $C_{3-7}$ cycloalkyl, phenyl, furyl, thienyl, pyridinyl or pyrazinyl, any of which groups may be optionally substituted; and R$^2$ represents $C_{3-7}$ cycloalkyl($C_{1-6}$)alkyl, aryl($C_{1-6}$)alkyl or heteroaryl($C_{1-6}$)alkyl, any of which groups may be optionally substituted.

2. The compound of claim 1 of the formula IIA, or a pharmaceutically acceptable salt thereof:

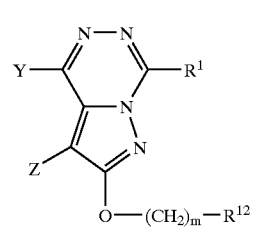

(IIA)

wherein m is 1 or 2; and

R$^{12}$ represents aryl or heteroaryl, either of which groups may be optionally substituted.

3. The compound of claim 2 of the formula IIB, or a pharmaceutically acceptable salt thereof:

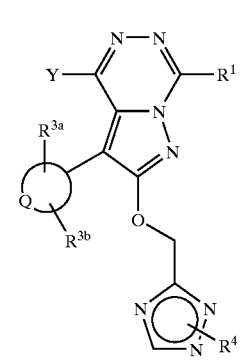

(IIB)

wherein

Q represents the residue of a cyclopropyl, cyclobutyl, cyclopentyl, cyclohexyl, phenyl, pyridinyl, furyl or thienyl ring;

R$^{3a}$ represents hydrogen, methyl, fluoro, chloro, trifluoromethyl, cyano or amino;

R$^{3b}$ represents hydrogen or fluoro; and

R$^4$ represents hydrogen, methyl, ethyl, n-propyl, isopropyl, fluoroethyl or difluoroethyl.

4. A compound selected from the group consisting of:

3,7-bis(2-fluorophenyl)-4-methyl-2-(2-methyl-2H-[1,2,4]triazol-3-ylmethoxy)pyrazolo[1,5-d][1,2,4]triazine;

3-(2-fluorophenyl)-4-methyl-2-(2-methyl-2H-[1,2,4]triazol-3-ylmethoxy)-7-phenylpyrazolo[1,5-d][1,2,4]triazine;

3-cyclopentyl-2-(2-ethyl-2H-[1,2,4]triazol-3-ylmethoxy)-7-(2-fluorophenyl)-4-methylpyrazolo[1,5-d][1,2,4]triazine;

3-cyclopentyl-7-(2-fluorophenyl)-4-methyl-2-(2-methyl-2H-[1,2,4]triazol-3-ylmethoxy)pyrazolo[1,5-d][1,2,4]triazine;

3-cyclopentyl-2-(2-ethyl-2H-[1,2,4]triazol-3-ylmethoxy)4-methyl-7-phenyl-pyrazolo[1,5-d][1,2,4]triazine;

3-cyclopentyl-4-methyl-2-(2-methyl-2H-[1,2,4]triazol-3-ylmethoxy)-7-phenylpyrazolo[1,5-d][1,2,4]triazine;

or a pharmaceutically acceptable salt thereof.

5. A compound selected from the group consisting of:

3-tert-butyl-7-(2,5-difluorophenyl)-2-(2-ethyl-2H-[1,2,4]triazol-3-ylmethoxy)-4-methylpyrazolo[1,5-d][1,2,4]triazine;

3-tert-butyl-4-methyl-2-(2-methyl-2H-[1,2,4]triazol-3-ylmethoxy)-7-(2,3,6-trifluorophenyl)pyrazolo[1,5-d][1,2,4]triazine;

3-(2-fluorophenyl)-4-methyl-2-(2-methyl-2H-[1,2,4]triazol-3-ylmethoxy)-7-(pyrazin-2-yl)pyrazolo[1,5-d][1,2,4]triazine;

3,7-bis(2-fluorophenyl)-4-methyl-2-(1-methyl-1H-[1,2,4]triazol-3-ylmethoxy)pyrazolo[1,5-d][1,2,4]triazine;

2-(2-ethyl-2H-[1,2,4]triazol-3-ylmethoxy)-3-(2-fluorophenyl)-4-methyl-7-(thien-3-yl)pyrazolo[1,5-d][1,2,4]triazine;

3-(2-fluorophenyl)-4-methyl-2-(1-methyl-1H-[1,2,4]triazol-3-ylmethoxy)-7-(thien-3-yl)pyrazolo[1,5-d][1,2,4]triazine;

3-cyclohexyl-7-(2-fluorophenyl)-4-methyl-2-(2-methyl-2H-[1,2,4]triazol-3-ylmethoxy)pyrazolo[1,5-d][1,2,4]triazine;

7-(2-fluorophenyl)-4-methyl-2-(2-methyl-2H-[1,2,4]triazol-3-ylmethoxy)-3-(thien-3-yl)pyrazolo[1,5-d][1,2,4]triazine;

7-(2-fluorophenyl)-4-methyl-2-(2-methyl-2H-[1,2,4]triazol-3-ylmethoxy)-3-phenylpyrazolo[1,5-d][1,2,4]triazine;

7-(2-fluorophenyl)-3-(fur-3-yl)-4-methyl-2-(2-methyl-2H-[1,2,4]triazol-3-ylmethoxy)pyrazolo[1,5-d][1,2,4]triazine;

7-(2-fluorophenyl)-4-methyl-2-(1-methyl-1H-[1,2,4]triazol-3-ylmethoxy)-3-(thien-3-yl)pyrazolo[1,5-d][1,2,4]triazine;

7-(2-fluorophenyl)-4-methyl-2-(1-methyl-1H-[1,2,3]triazol-4-ylmethoxy)-3-(thien-3-yl)pyrazolo[1,5-d][1,2,4]triazine;

7-(4-fluorophenyl)-4-methyl-2-(2-methyl-2H-[1,2,4]triazol-3-ylmethoxy)-3-(thien-3-yl)pyrazolo[1,5-d][1,2,4]triazine;

7-(2,4-difluorophenyl)-4-methyl-2-(2-methyl-2H-[1,2,4]triazol-3-ylmethoxy)-3-(thien-3-yl)pyrazolo[1,5-d][1,2,4]triazine;

or a pharmaceutically acceptable salt thereof.

6. A pharmaceutical composition comprising the compound of claim 1 or a pharmaceutically acceptable salt thereof in association with a pharmaceutically acceptable carrier.

7. A process for the preparation of the compound of claim 1 which comprises:

(A) cyclising a compound of formula III:

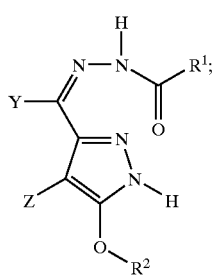

(III)

or (B) reacting a compound of formula VI with a compound of formula VII:

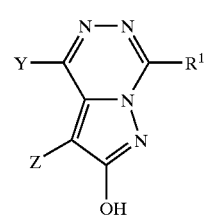

(VI)

$R^2$—$L^1$ (VII)

wherein $L^1$ represents a suitable leaving group; or (C) reacting a compound of formula IX with a compound of formula X:

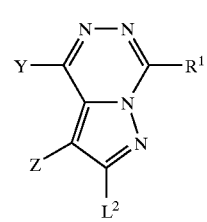

(IX)

$R^2$—OH (X)

wherein $L^2$ represents a suitable leaving group; or (D) reacting a compound of formula XII with a compound of formula XIII:

Z—M (XII)

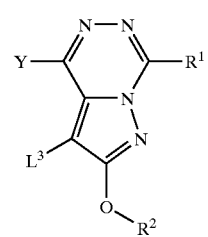

(XIII)

wherein $L^3$ represents a suitable leaving group, and M represents —B(OH)$_2$ or a cyclic ester thereof formed with an organic diol, or M represents —Sn(Alk)$_3$ in which Alk represents a $C_{1-6}$ alkyl group; in the presence of a transition metal catalyst; and (E) subsequently, if desired, converting a compound of formula I initially obtained into a further compound of formula I by standard methods.

8. A method for the treatment of anxiety which comprises administering to a patient in need of such treatment an effective amount of the compound of claim 1 or a pharmaceutically acceptable salt thereof.

* * * * *